(12) United States Patent
Giannotta et al.

(10) Patent No.: US 7,745,193 B2
(45) Date of Patent: Jun. 29, 2010

(54) HYBRID PROTEINS OF ACTIVE-SITE SERINE β-LACTAMASE

(75) Inventors: Fabrizio Giannotta, Waremme (BE); Patrice Filee, Jupille (BE); Moreno Galleni, Fraiture (BE); Jean-Marie Frere, Nandrin (BE); Bernard Joris, Spa (BE); Alain Brans, Beaufays (BE); Nadia Ruth, Liege (BE)

(73) Assignee: Universite de Liege, Angleur (BE)

( * ) Notice: Subject to any disclaimer, the term of this patent is extended or adjusted under 35 U.S.C. 154(b) by 522 days.

(21) Appl. No.: 10/589,233

(22) PCT Filed: Jan. 17, 2005

(86) PCT No.: PCT/EP2005/050174

§ 371 (c)(1), (2), (4) Date: Jan. 16, 2007

(87) PCT Pub. No.: WO2005/078075

PCT Pub. Date: Aug. 25, 2005

(65) Prior Publication Data

US 2007/0161040 A1 Jul. 12, 2007

(30) Foreign Application Priority Data

Feb. 11, 2004 (EP) .................... 04075430

(51) Int. Cl.
C12N 9/86 (2006.01)
C12N 9/14 (2006.01)
C12N 15/09 (2006.01)
C12P 21/06 (2006.01)
G01N 33/53 (2006.01)
C12Q 1/34 (2006.01)
C07H 21/04 (2006.01)

(52) U.S. Cl. .................... 435/231; 435/195; 435/183; 435/69.1; 435/69.7; 435/7.1; 435/18; 536/23.1; 536/23.2; 536/23.4

(58) Field of Classification Search .................... None
See application file for complete search history.

(56) References Cited

U.S. PATENT DOCUMENTS 5,830,457 A 11/1998 Gicquel et al.
2003/0165825 A1* 9/2003 Balint et al. .................... 435/6

FOREIGN PATENT DOCUMENTS

WO WO 03/105753 A2 12/2003

OTHER PUBLICATIONS

Broun et al., Catalytic plasticity of fatty acid modification enzymes underlying chemical diversity of plant lipids. Science, 1998, vol. 282: 1315-1317.*
Kisselev L., Polypeptide release factors in prokaryotes and eukaryotes: same function, different structure. Structure, 2002, vol. 10: 8-9.*
Wishart et al., A single mutation converts a novel phosphotyrosine binding domain into a dual-specificity phosphatase. J. Biol. Chem., 1995, vol. 270(45): 26782-26785.*
Witkowski eta l., Conversion of b-ketoacyl synthase to a Malonyl Decarboxylase by replacement of the active cysteine with glutamine. Biochemistry, 1999, vol. 38: 11643-11650.*
Backstrom, M. et al. (1995) "Characterization of an internal permissive site in the cholera toxin b-subunit and insertion of epitopes from human immunodeficiency virua-1, hepatitis b virus and enterotoxigenic *Escherichia coli*" *Gene* 165:163-171.
Galarneu, A. et al. (2002) "β-lactamase protein fragment complementation assays as in vivo and in vitro sensors of protein-protein interactions" *Nature Biotechnology* 20:619-622.
Hallet, B. et al. (1997) "Pentapeptide scanning mutagenesis: random insertion of a variable five amino acid cassette in a target protein" *Nucleic Acids Research* 25:1866-1867.
Hayes, F. et al. (1996) "Insertion mutagenesis as a tool in the modification of protein function" *The Journal of Biological Chemistry* 272:28833-28836.
Ruth, N. et al. (2005) "DNA vaccination for the priming of neutralizing antibodies against non-immunogenic STa enterotoxin from enterotoxigenic *Escherichia coli*" *Vaccine* 23:3618-3627.
Siemers, N. et al. (1997) "Construction, expression, and activities of L49-sFv-β-Lactamase, a single-chain antibody fusion protein for anticancer prodrug activation" *Bioconjugate Chem.* 8:510-519.
Ausubel, F.M. et al. in *Curent Protocols in Molecular Biology*, John Wiley & Sons, Inc. 1987-1994 and 1994-2009, Section 2.10, pp. 1-16.
Heritage, J. et al. 1999 "Evolution and spread of SHV extended-spectrum β-lactamases in gram-negative bacteria" *J Antimicrobial Chemotherapy* 44:309-318.

* cited by examiner

*Primary Examiner*—Ganapathirama Raghu
(74) *Attorney, Agent, or Firm*—Knobbe, Martens, Olson & Bear, LLP

(57) ABSTRACT

The present invention refers to a recombinant nucleotide sequence which codes upon expression for at least a part of a bifunctional hybrid active-site serine β-lactamase protein, wherein the β-lactamase protein is bearing at least one heterologous sequence, wherein in that the hybrid protein is having two functions, the first function is associated with the β-lactamase portion and the second function is associated with the heterologous sequence having a biological function which is different from the first function.

12 Claims, 21 Drawing Sheets

Fig. 3

TEM-1
WT
Leu Leu Thr Gly Glu Leu Leu Thr Leu Ala
CTA-TTA-ACT-GGC-GAA-CTA-CTT-ACT-CTA-GCT

TEM-1
197 KpnI
Leu Leu Thr Gly *Val Pro Leu Thr* Gly Thr Leu Ala
CTA-TTA-ACT-GGG-GTA-CCC-CTA-ACT-GGC-ACT-CTA-GCT
          <u>KpnI</u>

TEM-1
197
cartridge 1
Leu Leu Thr Gly *Val Pro Pro Gly* Leu Gln Leu Glu Leu Lys Pro Gly Arg Tyr Pro Leu Thr Gly Glu Leu
CTA-TTA-ACT-GGG-GTA-CCG-CCC-GGG-CTG-CAG-CTC-GAG-CTT-AAG-CCC-GGG-CGG-TAC-CCC-CTA-ACT-GGC-GAA-CTA
          <u>KpnI  SmaI   PstI  XhoI  AflII  SmaI      KpnI</u>

TEM-1
197
cartridge 2
Leu Leu Thr Gly *Val Pro Pro Gly* Arg Tyr Pro Leu Thr Gly Glu Leu
CTA-TTA-ACT-GGG-GTA-CCG-CCC-GGG-CGG-TAC-CCC-CTA-ACT-GGC-GAA-CTA
          <u>KpnI  SmaI       KpnI</u>

Fig. 4

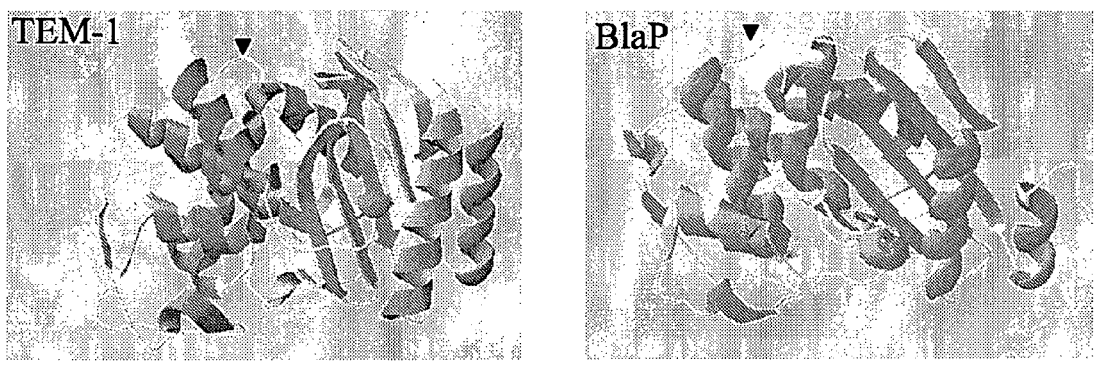

Fig. 5

| | | | | | | | | | | |
|---|---|---|---|---|---|---|---|---|---|---|
| BlaP Wt | Ala GCT | Leu CTT | Glu GAA | Asp GAT | Lys AAA | Leu CTT | Pro CCA | Ser AGT | Glu GAA | Lys AAA |
| BlaP 211 SmaI | Ala GCT | Leu CTT | Glu GAA | Asp GAT | *Pro* CCC | *Gly* GGG | Lys AAA | Leu CTT | Pro CCA | Ser AGT | Glu GAA | Lys AAA |

*SmaI*

| | | | | | | | | | | |
|---|---|---|---|---|---|---|---|---|---|---|
| BlaL WT | Val GTC | Glu GAG | Asp GAC | Gly GGC | Glu GAG | Lys AAG | Ala GCC | Ala GCC | Leu CTC | Ala GCG |
| BlaL 203 SmaI | Val GTC | Glu GAG | Asp GAC | Gly GGC | Glu GAG | *Asp* GAT | *Ile* ATC | Lys AAG | Ala GCC | Ala GCC | Leu CTC | Ala GCG |

*EcoRV*

Fig. 12 A, B, C
A
| S | E | D | A | B | C | P |
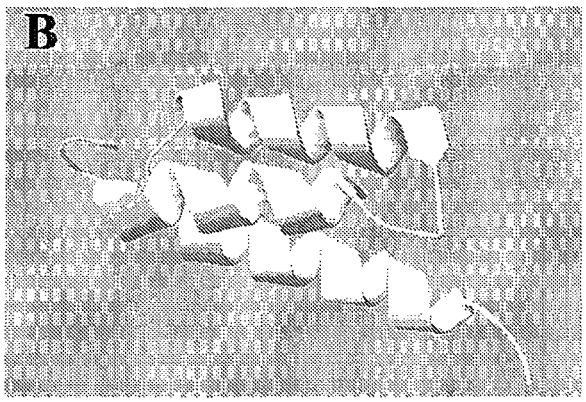

Fig. 12 D, E
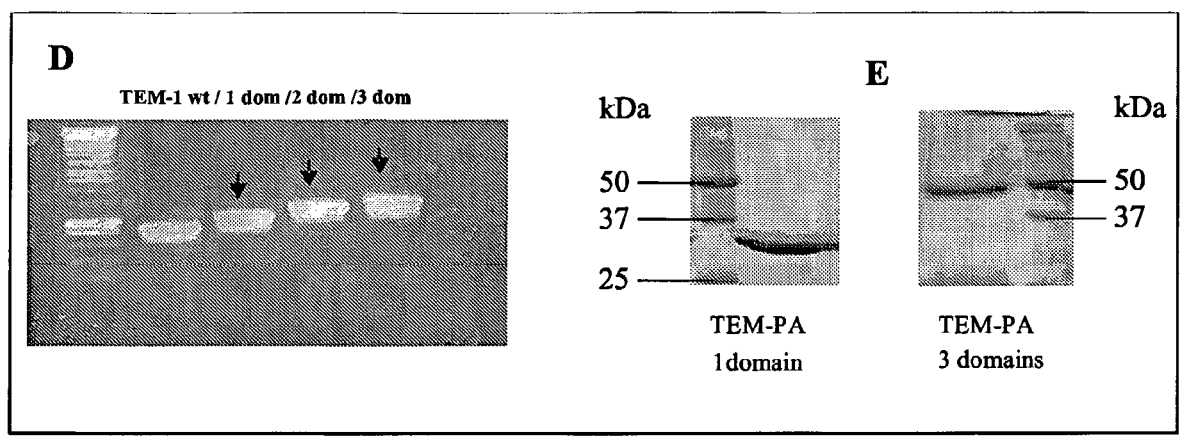

Fig. 13
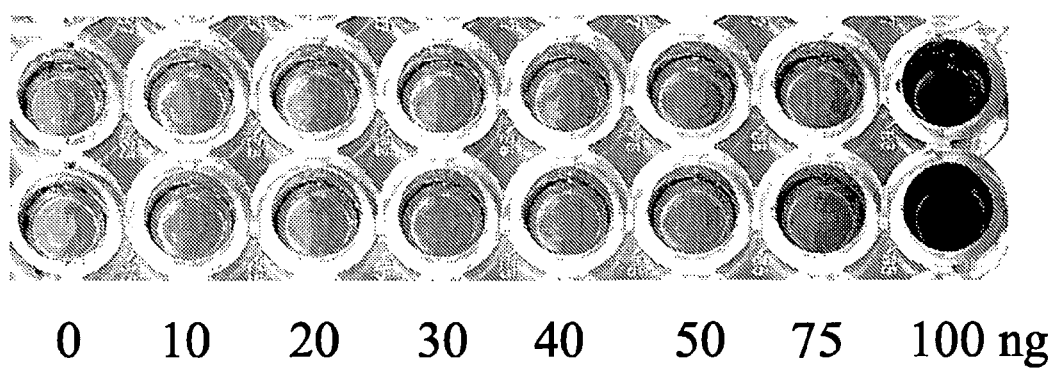
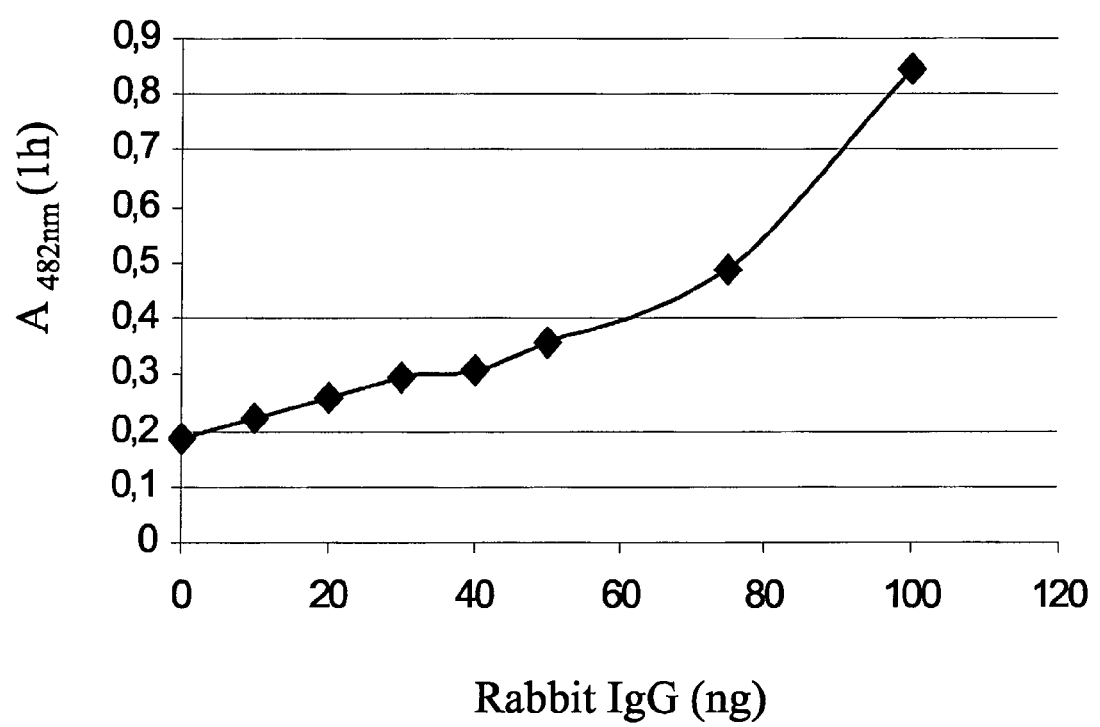

Figure 14 A B C D
S  B1  B2
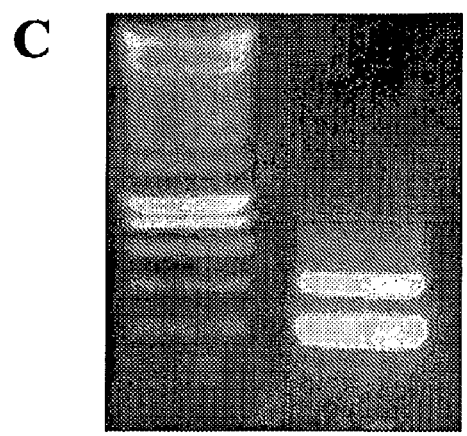
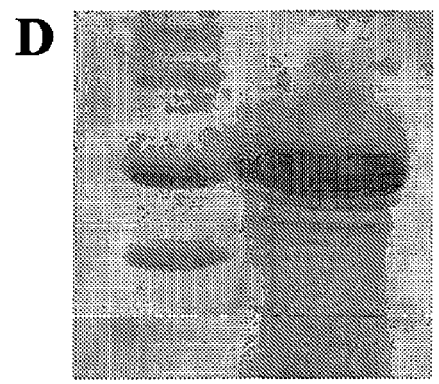

Fig. 15

BlaP Wt  Ala Leu Glu Asp Lys Leu Pro Ser Glu Lys
GCT-CTT-GAA-GAT-AAA-CTT-CCA-AGT-GAA-AAA

BlaP HA  Ala Leu Glu Asp Pro Arg Phe Tyr Pro Tyr Asp Val Pro Asp Tyr Ala Thr Thr Gly Lys Leu Pro Ser Glu Lys
GCT-CTT-GAA-GAT-CCC-AGG-TTT-TAT-CCA-TAC-GAC-GTC-CCG-GAC-TAC-GCC-ACA-ACT-GGG-AAA-CTT-CCA-AGT-GAA-AAA

HYBRID PROTEINS OF ACTIVE-SITE SERINE β-LACTAMASE

RELATED APPLICATIONS

This application is a US National Phase of International Application No.: PCT/EP2005/050174, filed Jan. 17, 2005, designating the US and published in English on Aug. 25, 2005 as WO 2005/078075, which claims the benefit of European application No.: 04075430.1, filed Feb. 11, 2004, the entire disclosure of which is hereby expressly incorporated by reference.

FIELD OF THE INVENTION

The present invention relates to hybrid proteins of active-site serine β-lactamase.

BACKGROUND OF THE INVENTION

In the state of art a plurality of scientific publications have described the construction of fusion proteins. In the majority of these cases, such fusion proteins were realised as fusions of polypeptides to the N-terminus or C-terminus of a carrier protein. Martineau et al. (Martineau, P., J. G. Guillet, et al. (1992). "Expression of heterologous peptides at two permissive sites of the MalE protein: antigenicity and immunogenicity of foreign B-cell and T-cell epitopes." Gene 118(1): 151; Martineau, P., C. Leclerc, et al. (1996). "Modulating the immunological properties of a linear B-cell epitope by insertion into permissive sites of the MalE protein." Mol Immunol 33(17-18): 1345-58.) have realized the insertion of a protein into permissive sites of the protein MalE and they have studied the immune response against the inserted protein.

Several authors describe the immunisation against the enterotoxins STa (heat stable enterotoxin of *E. coli*) via constructing N-terminal or C-terminal fusion proteins, wherein different carrier proteins are involved, in order to obtain an immune response against the STa peptide, which as such is not immunogenic. The construction of hybrid proteins by inserting the STa peptide into a permissive site of a carrier protein has not yet been described in the prior art. The β-lactamase TEM-1 also not has been used as carrier protein for the construction of hybrid or fusion proteins with STa.

The process for synthesising bifunctional proteins got underway through binding one protein to another by chemical means. Against the background of this approach, the two proteins of interest, which have different properties, are synthesised independently and then treated with a chemical so as to achieve the covalent bonding of specific chemical groups available in the proteins. The technique has helped to achieve progress in developing diagnosis tests and recombinant vaccines. However, it has several drawbacks that have prompted the scientific community to develop other options. One of the disadvantages of using chemical agents is the aspecific coupling of two target proteins, which results in a lack of uniformity in the way the two proteins are bad associated and oriented. This in turn may inactivate one of the proteins. As a result of the binding system, protein complexes are formed where the stoichiometry and composition is heterogeneous. For example, a protein X may be associated with one, two, three or more Y proteins. A binding between identical molecules (dimer-multimer) is difficult to avoid, thereby reducing the quantity of bifunctional proteins obtained. The resulting assay challenges can be intuitively understood, along with the calibration stage required to assess the sensitivity of the product with each further coupling.

Another challenge with the aspecific binding of the bridging agents is that these techniques call for large quantities of proteins in return for a reduced yield potential, thereby pushing up the costs of the finished product. A de novo synthesis of bifunctional proteins in prokaryotics or eukaryotics systems offers an alternative way of meeting these challenges. This method involves molecular biology techniques providing an opportunity to modify the structure of the coding gene for the proteins in question. However, this technology calls for a detailed knowledge of the biochemical and structural properties of the polypeptides synthesised on the basis of their manipulated sequence of nucleotides.

An initial de novo synthesis approach was adopted on the basis of fusion proteins. This involves genetically fusing coding DNA sequences for two proteins of interest to one or the other ends of the said genes. This fusion operation may apply to whole proteins, fragments of proteins or random peptides. The two proteins (or protein fragments) are then expressed in tandem by the producer organism. This technique solves the problems of difficult, insoluble, misfolding proteins. It also addresses issues related to chemical coupling (see above), even though it is not the technique by which other ones are judged in this sphere. Presenting a peptide to the ends of another protein means this protein is exposed to excessive proteolysis when the fusion protein is being produced and purified. What is more, the degrees of freedom of the fusion peptides are such that they seriously destabilise the structure of the entire fusion. The result is a total loss of biological activity.

Therefore it was object of the present invention to provide functional proteins wherein the respective carrier protein retains its activity and also the added heterologous sequence still processes its function (for example as epitope, enzyme etc.), wherein furthermore the added heterologous sequence is somehow exposed on the surface of the carrier protein which is providing the possibility that the heterologous sequence may interact with other molecules. Furthermore, it was the object of the present invention to provide the functional proteins wherein the additional heterologous sequence maintains its free dimensional structure. It was a further object that the heterologous sequence is made less susceptible to proteolysis.

SUMMARY OF THE INVENTION

The object of the present invention is solved by a recombinant nucleotide sequence which codes upon expression for at least a part of a bifunctional hybrid active-site serine β-lactamase protein, wherein the β-lactamase protein is bearing at least one heterologous sequence, wherein the hybrid protein is having two functions, the first function is associated with the β-lactamase portion and the second function is associated with the heterologous sequence having a biological function which is different from the first function.

In a preferred embodiment the β-lactamase protein is having conserved amino acid elements 1, 2 and 3, wherein element 1 is having the amino acid sequence SXXK, element 2 is having the amino acid sequence SDN in class A proteins, YXN in class C proteins, SX[V or T or N] in class D proteins, wherein the elements of classes A, C and D correspond to each other, and element 3 is having the amino acid sequence K[T or S]G, wherein the β-lactamase protein is bearing at least one heterologous sequence between element 2 and element 3. Element 1 is the conserved sequence containing the serine of the active site and always located at the N-terminus of the alpha2 helix. Element 2 is the SDN loop of class A, corresponding to YXN and SX[V or T or N] in class C and D, respectively. This loop is located between helices alpha4 and alpha 5 in class A β-lactamases. In class A, the serine seems to be involved in maintaining the functional positioning of the two domains (the all alpha and the alpha/beta domains). The tyrosine at position 150 in class C β-lactamase could act as a general base in the catalytic phenomenon. Element 3 is located on the β-strand domain of the β-lactamase facing the second element.

Further preferred, the β-lactamase protein is bearing at least one heterologous sequence in a region located between two neighboring alpha helices of the β-lactamase sequence, wherein the region is forming a juncture between the alpha helices of active-site serine β-lactamases, wherein said alpha helices correspond to the last two alpha helices before the alpha/beta domain. The active-site serine β-lactamases of classes A, C and D have a two domain structure: one domain is the alpha domain containing alpha helices only; the other domain is the alpha/beta domain containing alpha helices and beta sheets. The loop between the last two alpha helices of the first domain (the all alpha helices domain) is the preferred insertion site of the heterologous sequence according to the present invention. In TEM-1 β-lactamase, which is a class A β-lactamase, these last two alpha helices of the all alpha domain are alpha helix 8 and alpha helix 9, which are before the alpha/beta domain. Due to the high similarity between class A, C and D β-lactamases on a three-dimensional level, these helices and their loop in between (as insertion site) can be identified in any β-lactamase of any of the three classes A, C and D.

Furthermore, it is preferred the β-lactamase protein is bearing at least one heterologous sequence in a region located between two neighboring alpha helices of the β-lactamase sequence, wherein the region is selected from:
  a) the region forming a juncture between alpha helix 8 and alpha helix 9 of TEM-1 β-lactamase;
  b) the region forming a juncture between the alpha helices which are homologous to alpha helix 8 and alpha helix 9 of TEM-1 β-lactamase.

In another preferred embodiment the β-lactamase moiety is selected from the group:
  a) class A β-lactamase,
  b) class C β-lactamase,
  c) class D β-lactamase,
  d) a recombinant sequence of one or more of a) to c).

In one alternative embodiment the β-lactamase moiety is derived from class A β-lactamase, wherein β-lactamase class A protein is bearing the heterologous sequence in the region forming a juncture between alpha helix 8 and alpha helix 9. More preferred the region forming a juncture between alpha helix 8 and alpha helix 9 is selected from the group:
  a) the amino acid sequence Thr195 to Leu199 of the TEM-1 β-lactamase;
  b) the amino acid sequence corresponding to the amino acid sequence Thr195 to Leu199 in TEM-1 β-lactamase.

The amino acid sequence corresponding to the amino acid sequence Thr195 to Leu199 in TEM-1 β-lactamase is located between the last two alpha helices of the all alpha domain. In class A β-lactamase these helices are helix 8 and helix 9. The alpha helices 8 and 9 are defined as sequences ARALATSLQAFA (SEQ ID NO: 42) and SEKRELLID-WMK (SEQ ID NO: 43) in BlaP and are defined as PAAMAT-TLRKLL (SEQ ID NO: 44) and LASRQQLIDWME (SEQ ID NO: 45) in TEM-1 β-lactamases, respectively, and those alpha helices which correspond to those in β-lactamases of the same class or of classes C and D.

In another alternative embodiment the β-lactamase moiety is derived from class C β-lactamase, wherein β-lactamase class C protein is bearing the heterologous sequence in the region forming a juncture between alpha helices, which correspond to alpha helix 8 and alpha helix 9 in TEM-1 β-lactamase.

In a further alternative embodiment the region forming a juncture is selected from the group:
  a) the amino acid sequence K239 to E245 of the AmpC β-lactamase;
  b) the amino acid sequence corresponding to the amino acid sequence K239 to E245 of the AmpC β-lactamase.

The amino acid sequence corresponding to the amino acid sequence K239 to E245 of the AmpC β-lactamase is located between the last two alpha helices of the all alpha domain. In class C β-lactamase these helices, which correspond to helix 8 and helix 9 of class A β-lactamases, are defined as sequences IEDMARWVQSNL (SEQ ID NO: 46) and KTLQQGIQLA (SEQ ID NO: 47).

In a further alternative embodiment the β-lactamase moiety is derived from class D β-lactamase, wherein β-lactamase class D protein is bearing the heterologous sequence in the region forming a juncture between alpha helices, which correspond to alpha helix 8 and alpha helix 9 in TEM-1 β-lactamase. In a preferred embodiment the region forming a juncture is selected from the group:
  a) the amino acid sequence N510 to Q516 of the BlaR-CTD β-lactamase;
  b) the amino acid sequence corresponding to the amino acid sequence N510 to Q516 of the BlaR-CTD β-lactamase.

The amino acid sequence corresponding to the amino acid sequence N510 to Q516 of the BlaR-CTD β-lactamase. In class D β-lactamase these helices, which correspond to helix 8 and helix 9 of class A β-lactamases, are defined as sequences SPLEQVNILKKFYD and KQSNIETVKDSI, respectively, in BlaR-CTD, and defined by alpha helices which correspond to those in β-lactamases of the same class or of classes A and C.

The following table is showing the positions of the two helices helix 8 and helix 9 in different β-lactamases of class A, C and D enzymes.

TABLE 1

Comparison of corresponding helices 8 and 9 in β-lactamases. The numbering scheme for amino acids is according to ABL (see text). BlaP (SEQ ID NO: 5); TEM-1 (SEQ ID NO: 4); AmpC (SEQ ID NO: 38); BlaR-CTD (SEQ ID NO: 40).

|  | Helix 8 (grey highlight) | | Helix 9 (underlined only) | | Example for an |
|---|---|---|---|---|---|
|  | start | end | start | end | insertion site |
| BlaP | Ala 183 | Ala 194 | Ser 201 | Lys 212 | Asp 197 |
| TEM-1 | Pro 183 | Leu 194 | Leu 201 | Glu 212 | Glu 197 |

TABLE 1-continued

Comparison of corresponding helices 8 and 9 in β-lactamases. The numbering scheme for amino acids is according to ABL (see text). BlaP (SEQ ID NO: 5); TEM-1 (SEQ ID NO: 4); AmpC (SEQ ID NO: 38); BlaR-CTD (SEQ ID NO: 40).

|  | Helix 8 (grey highlight) | | Helix 9 (underlined only) | | Example for an |
|---|---|---|---|---|---|
|  | start | end | start | end | insertion site |
| AmpC | Ile 227 | Leu 238 | Lys 246 | Ala 255 | Leu 241 |
| BlaR-CTD | Ser 496 | Asp 509 | Lys 515 | Ile 526 | Phe 514 |

BlaP (bold: signal peptide)
```
mklwfstlkl kkvaavllfs cvalagcgsn hsnashsaek dektemkddf akleeqfdak
lgifaldtgt nrtvtyrpde rfafastika ltvgvllqqk siedlnqrit ytrddlvnyn
pitekhvdtg mtlkeladas lrysdntaqn lilkqiggpe slkkelrkig devtnperfe
pelnevnpge tqdtstarai atsiqafale dklpsekrel lidwmkrntt gdaliragvp
egwevadktg agsygtrndi aiiwppkgdp vvlavlssrd kkdakyddkl iaeatkvvvk
alnmesk
```

TEM-1 (bold: signal peptide)
```
msiqhfrval ipffaafclp vfahpetlvk vkdaedqlga rvgyieldln sgkilesfrp
eerfpmmstf kvllcgavls rvdagqeqig rrihysqndl veyspvtekh ltdgmtvrel
csaaitmsdn taanllltti ggpkeltafl hnmgdhvtrl drwepelnea ipnderdttm
paamattlrk lltgelltla srqqlidwme adkvagpllr salpagwfia dksgagergs
rgiiaalgpd gkpsrivviy ttgsqatmde rnrqiaeiga slikhw
```

AmpC (bold: signal peptide)
```
mfkttlcall itascstfaa pqqindivhr titplieqqk ipgmavaviy qgkpyyftwg
yadiakkqpv tqqtlfelgs vsktftgvlg gdaiargeik lsdpttkywp eltakqwngi
tllhlatyta gglplqvpde vksssdllrf yqnwqpawap gtqrlyanss iglfgalavk
psglsfeqam gtrvfqplkl nhtwinvppa eeknyawgyr egkavhvspg aldaeaygvk
stiedmarwy qsnikpldin ektlqqgiql aqsrywqtgd myqglgweml dwpvnpdsii
ngsdnkiala arpvkaitpp tpavraswvh ktgatggfgs yvafipekel givmlankny
pnparvdaaw qilnalq
```

BlaR-CTD
```
346       MQKET
351       RFLPGTNVEY EDYSTFFDKF SASGGFVLFN SNRKKYTIYN RKESTSRFAP
401       ASTYKVFSAL LALESGIITK NDSHMTWDGT QYPYKEWNQD QDLFSAMSSS
451       TTWYFQKLDR QIGEDHLRHY LKSIHYGNED FSVPADYWLD GSLQISPLEQ
501       VNILKKPYDN EFDFKQSNIE TVKDSIRLEE SNGRVLSGKT GTSVINGELH
551       AGWFIGTVET ADNTFFFAVH IQGEKRAAGS SAAEIALSIL DKKGIYPSVS
601       R
```

The numbering scheme of the amino acids sequences in table 1 is according to Amber, R. P., A. F. Coulson, J. F. Frére, J. M. Ghuysen, M. Forsman, B. Joris, R. Levesque, G. Tiraby, and S. G. Waley. 1991. A standard numbering scheme for the class A β-lactamases. Biochem. J. 276: 269-270. The BlaR protein is organized as a two-domain protein, including an N-terminal domain [BlaR-NTD, from residues 1 to 345] anchored into the membrane and an extracellular C-terminal domain [BlaR-CTD, from residues 346 to 601]. This latter, belongs to the serine penicillin-recognizing protein family and display the same 3-dimensional structure as class A β-lactamase. This is the reason why the sequence presented in table 1 begins at position 346.

The object of the present invention is also solved by a recombinant nucleotide acid sequence which codes upon expression for at least a part of a bifunctional hybrid β-lactamase class A protein, wherein the β-lactamase class A protein is bearing at least one heterologous sequence in a region located between two neighbouring alpha helices of the β-lactamase sequence, wherein the region is selected from:
  a) the region forming a juncture between alpha helix 8 and alpha helix 9 of the TEM-1 β-lactamase;
  b) the region forming a juncture between the alpha helices of homologous β-lactamases class A, said alpha helices corresponding to the alpha helix 8 and alpha helix 9 of the TEM-1 β-lactamase.

In a preferred embodiment the hybrid β-lactamase is possessing an activity selected from
  a) hydrolysing β-lactams;
  b) binding covalently and in a stable manner to derivatives of β-lactams and inhibitors of β-lactamases.

In a further preferred embodiment the hybrid protein is having two functions, the first function is associated with the β-lactamase portion and is selected from
  a) hydrolyzing β-lactams β-lactamase activity);
  b) binding covalently and in a stable manner to substances selected from
    the group β-lactams, derivatives of β-lactams, inhibitors of β-lactams;

wherein the second function is associated with the heterologous sequence having a biological function which is different from the first function.

According to the present invention the β-lactamase portion retains its activity, even after the homologous sequences is inserted. Although the degree of the activity might vary, the β-lactamase portion will have the same kind of activity as before the insertion. For example, if the β-lactamase was able to catalyse the cleavage of β-lactams, this activity will be maintained even after insertion. If a mutant β-lactamase is used which binds covalently to β-lactams and/or derivatives thereof, but does not catalyse the cleavage completely, then also this kind of mutant activity will be maintained after insertion of the heterologous sequence. The latter activity is useful to immobilize β-lactamase and hybrid β-lactamase, respectively, on carriers containing bound β-lactam substances.

Furthermore it is preferred that the hybrid β-lactamase retains its activity of hydrolysing β-lactams at least partially.

DETAILED DESCRIPTION OF THE DRAWINGS

FIG. 1 shows the 3D structure of TEM-1 β-lactamase. A: active site of the enzyme. B: highly tolerant position to exogenous polypeptide insertion.

FIG. 2 shows the model of β-lactamase hydrolysis of penicillin substrate.

FIG. 3 shows the sequence of restriction cassettes internalised in TEM-1 coding sequence. TEM-1 WT (SEQ ID NOs: 48 and 49); TEM-1 197 KpnI (SEQ ID NOs: 50 and 51); TEM-1 197 cartridge 1 (SEQ ID NOs: 52 and 53); TEM-1 197 cartridge 2 (SEQ ID NOs: 54 and 55).

FIG. 4 shows the 3D structures of TEM-1 and BlaP β-lactamases. Arrows show the polypeptide insertion site.

FIG. 5 shows the sequence of SmaI and EcoRV restriction site introduced in BlaP and BlaL coding sequence, respectively. BlaP Wt (SEQ ID NOs: 56 and 57); BlaP 211 SmaI (SEQ ID NOs: 58 and 59); BlaL WT (SEQ ID NOs: 60 and 61); BlaL 203 SmaI (SEQ ID NOs: 62 and 63).

Figure 8A:
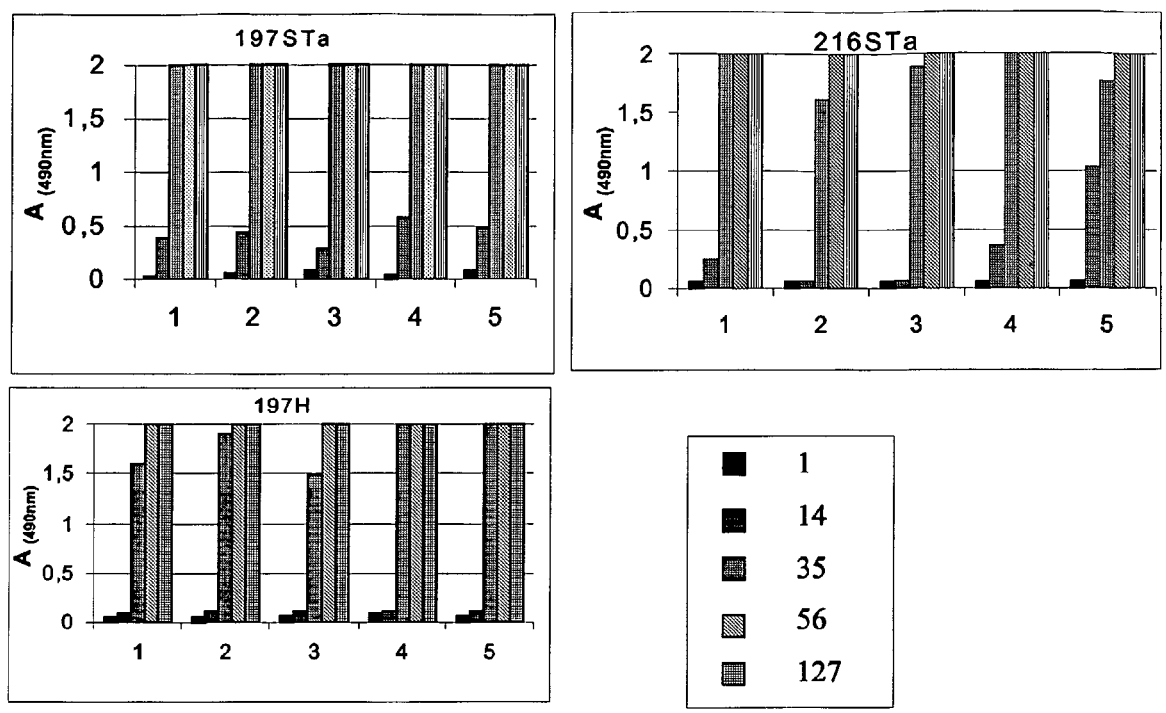
Figure 8B:
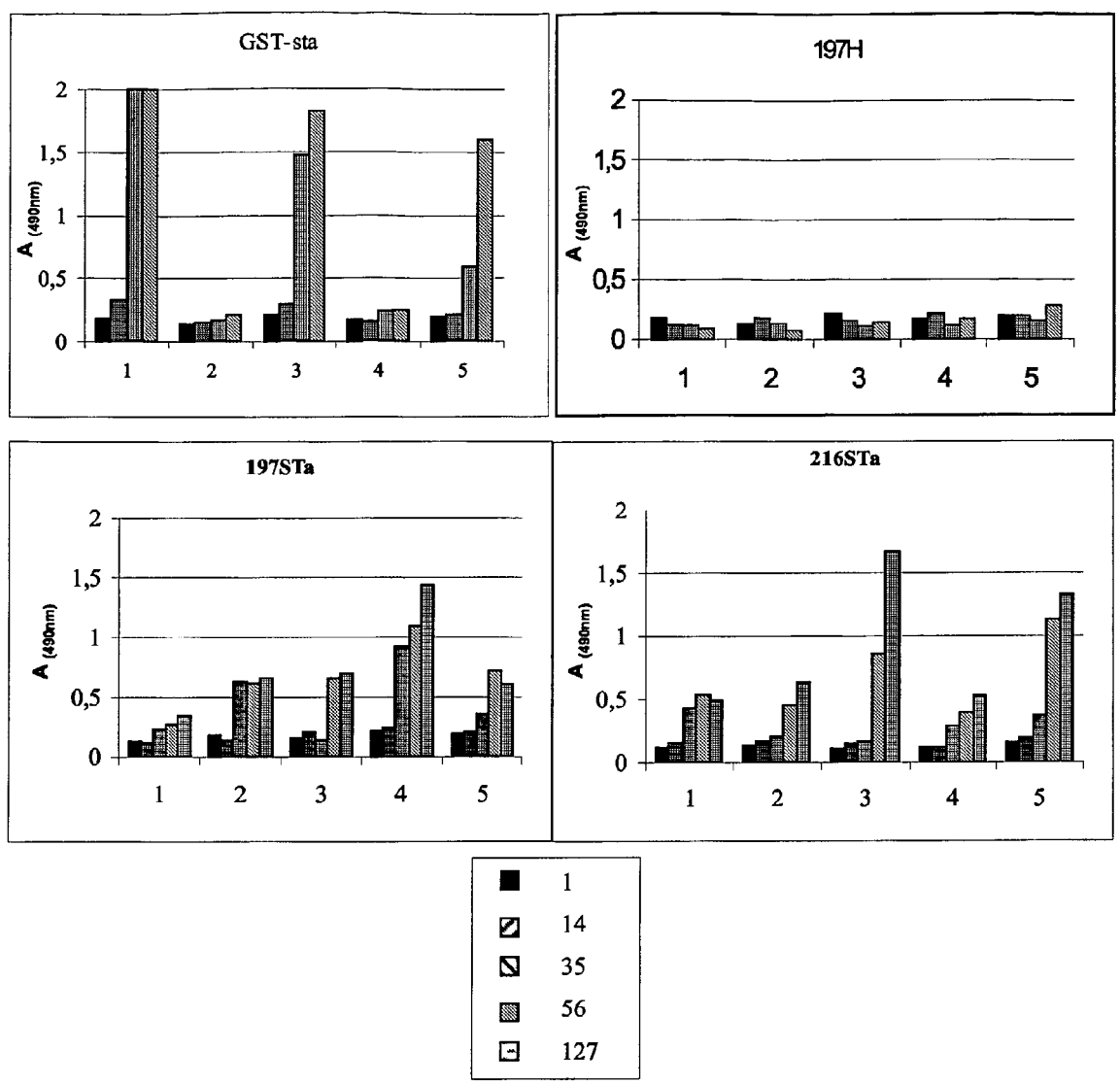

FIG. 8 shows the immunogenicity determined by ELISA for the TEM197H and TEM197STa. A) The presence of anti-TEM antibodies was estimated by coating 250 ng of TEM per well. B) The presence of anti-STa antibodies was estimated by coating 250 ng of GST-STa per well. The serum was diluted 100 fold in PBS buffer. The numbers below the columns of the diagram indicate different mouse individuals.

Figure 9:
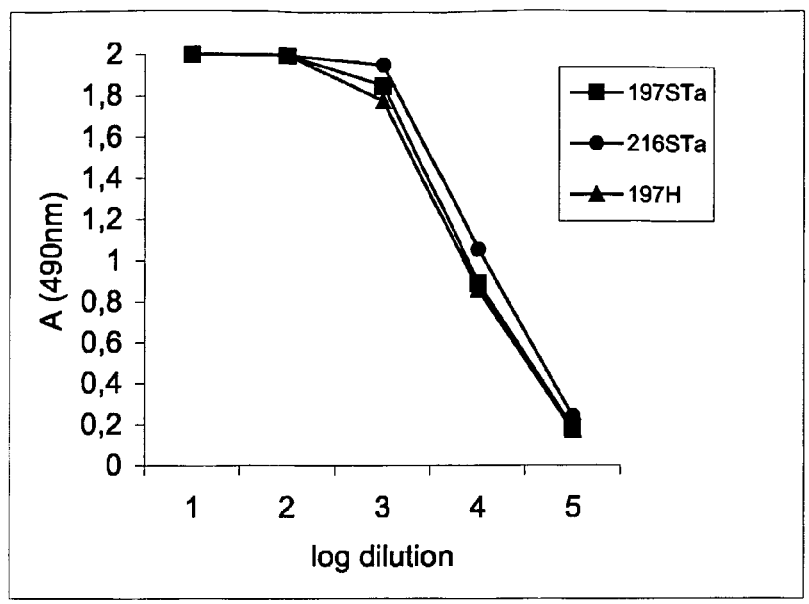

FIG. 9 shows the titration curve of the anti-TEM IgG in the serum collected at day 56.

Figure 10:
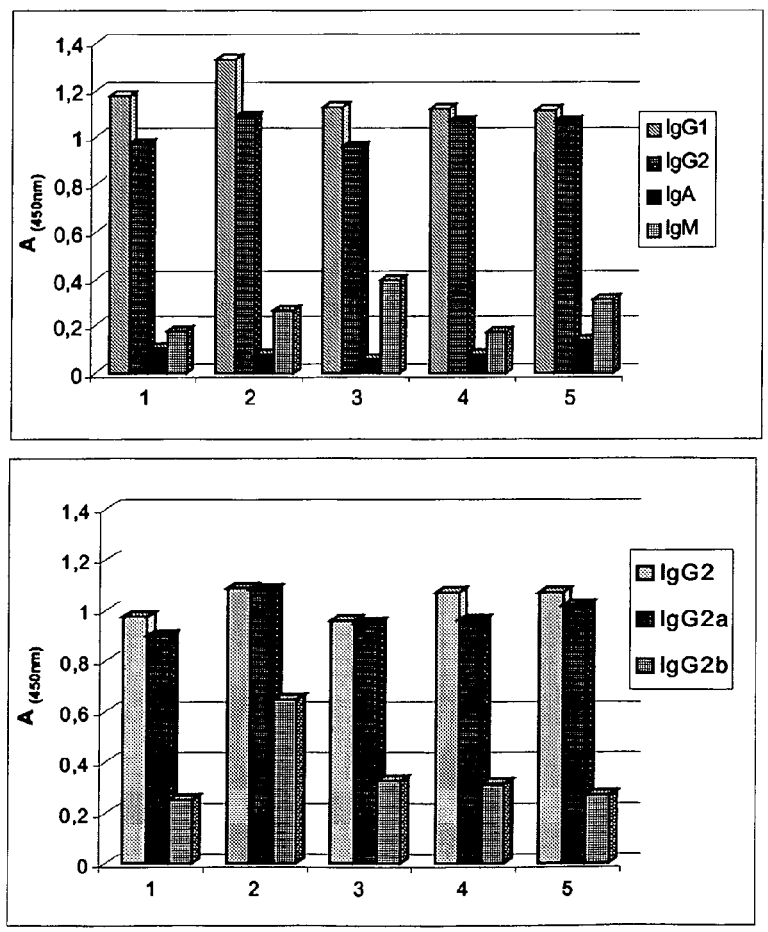

FIG. 10 shows the isotypic response against the carrier protein (TEM197H). The numbers below the columns of the diagram indicate different mouse individuals.

Figure 11:
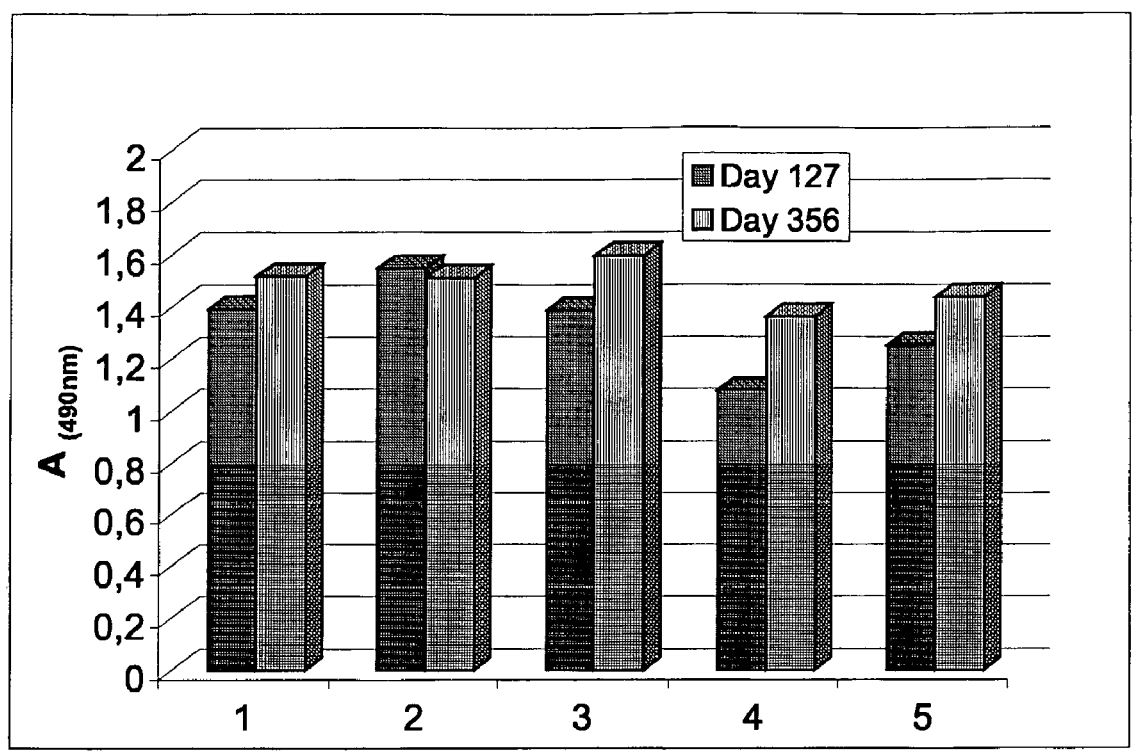

FIG. 11 shows the determination of the level of the anti-TEM IgG raised against TEM197H (1), TEM197STa (2), TEM216STa (3), TEM232STa (4) and TEM260STa (5). The numbers below the columns of the diagram indicate different mouse individuals.

FIG. 12 shows the construction of hybrid proteins of the TEM-1 β-lactamase wherein one or more repeated domains of the *Staphylococcus aureus* protein A (FIG. 12A) are internalised. A: protein A of *Staphylococcus aureus* is composed of five repeated domains indicated by letters E, D, A, B and C. These domains bind the antibody Fc region. S is the signal sequence. The sequence at the C-terminus is the peptidoglycan fixation domain (P). B: shows the structure of the E domain. Each of the repeated domains of protein A is organised into three α helices. C: the DNA coding for the repeated domains of protein A was amplified by PCR. D: the agarose gel is showing restriction analysis of different hybrid β-lactamase clones bearing 1, 2 or 3 domains of protein A. E: the SDS-PAGE gel analysis shows the hybrid β-lactamase proteins wherein one or three domains of protein A have been incorporated.

FIG. 13 shows the titration curve of immobilised rabbit IgG by TEM-PA hybrid protein. The absorbance is plotted against the amount of fixed rabbit IgG (ng).

FIG. 14 shows the construction of the hybrid proteins of the TEM-1 β-lactamase where the B1 and/or B2 domain or domains of the *Streptococcus pyogenes* protein G were internalised. A shows that protein G is composed of 2 repeated domains, called B1 and B2 that bind to the antibody Fc region. They confer an affinity for the antibodies Fc region. S is the signal peptide sequence of protein G. B shows that each of the 2 domains is organised with a β-sheet and α-helices. C shows that the nucleotide sequence encoding for the repeated domains of the G protein were cloned into the TEM-1 β-lactamase sequence. D shows an SDS-PAGE of hybrid β-lactamase TEM-1 having 2 domains of protein G internalised.

FIG. 15 shows the nucleotide sequence of insertion site of BlaP β-lactamase (SEQ ID NOs: 64 and 65) and BlaP-HA hybrid protein (SEQ ID NOs: 66 and 67).

Figure 16:
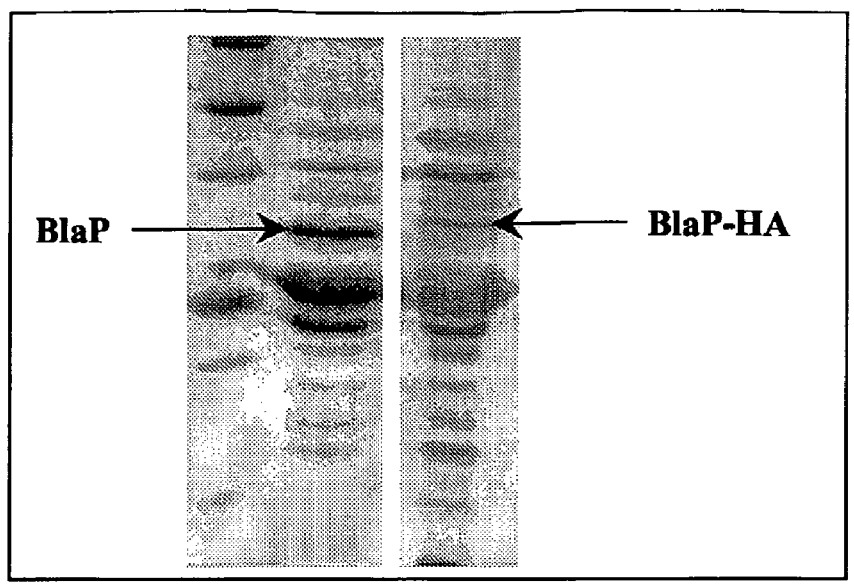

FIG. 16 shows a 12% SDS-PAGE gel electrophoresis of the BlaP and BlaP-HA β-lactamases after SFF partial purification of periplasmic fractions coming from *E. coli* strain transformed with pROGENO-1 BlaP(211/SmaI) and pROGENO-1 BlaP-HA. Transformed bacteria were grown over night on rich medium at 37° C.

Figure 17:
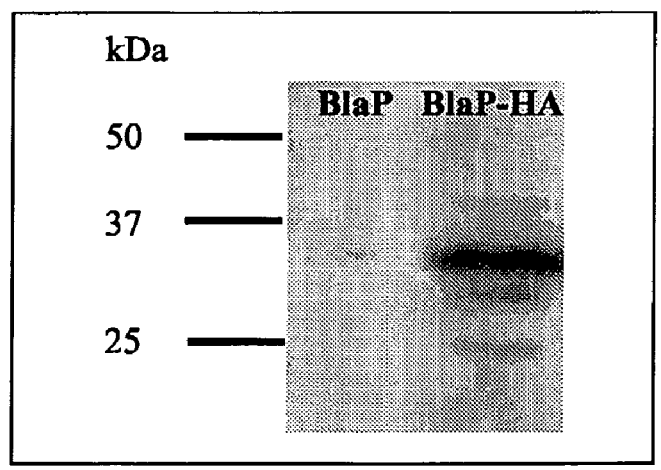

FIG. 17 shows a Western Blot analysis of the BlaP and BlaP-HA β-lactamases using monoclonal anti-HA antibody conjugated with peroxidase. Immunorecognised proteins were visualised by enhanced chemiluminescence detection.

Figure 18:
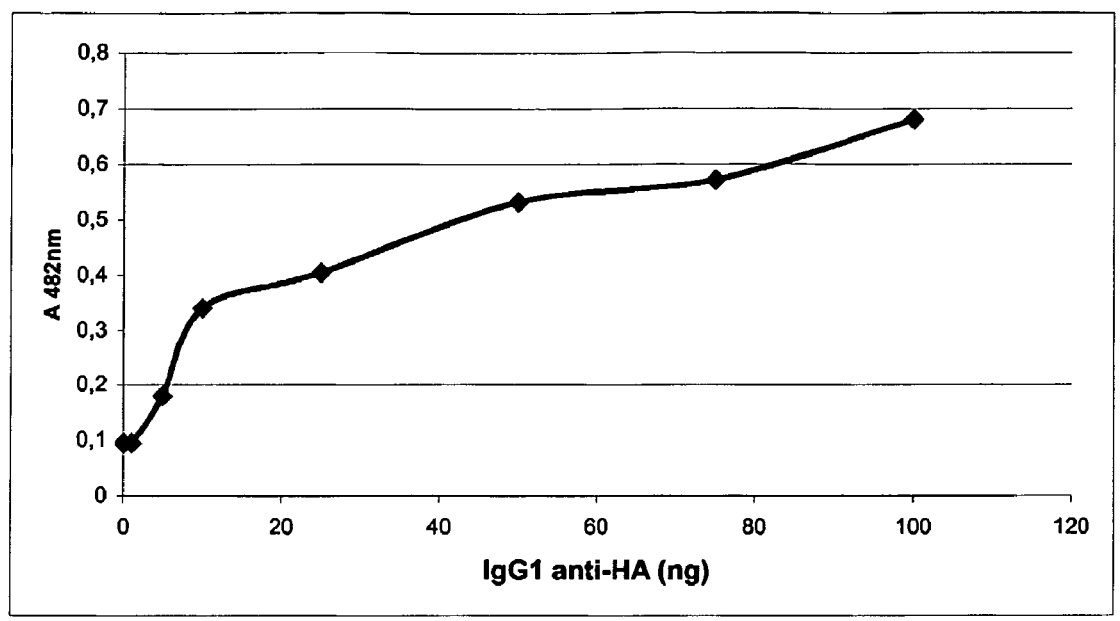

FIG. 18 shows the titration curve of immobilised rat IgG by BlaP-HA hybrid protein. The absorbance is plotted against the quantity of IgG1 of rat anti-HA in ng.

Figure 19:
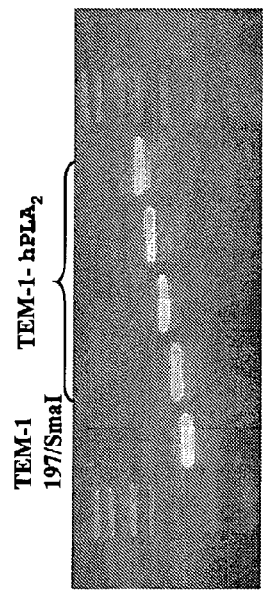

FIG. 19 shows the agarose gel where PCR amplification products of TEM-1 (197/SuraI) and some hybrid TEM-1 hPLA$_2$ protein were loaded.

Figure 20:
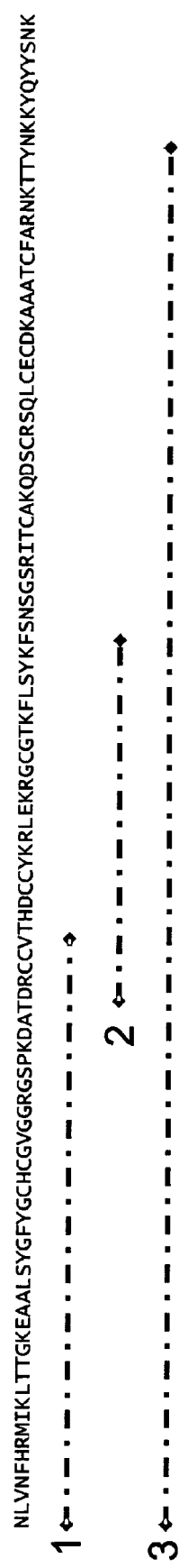

FIG. 20 shows the primary structure of the hPLA$_2$ (SEQ ID NO: 68) on which the various fragments internalised in TEM-1 are underlined (1, 2 and 3).

Figure 21:
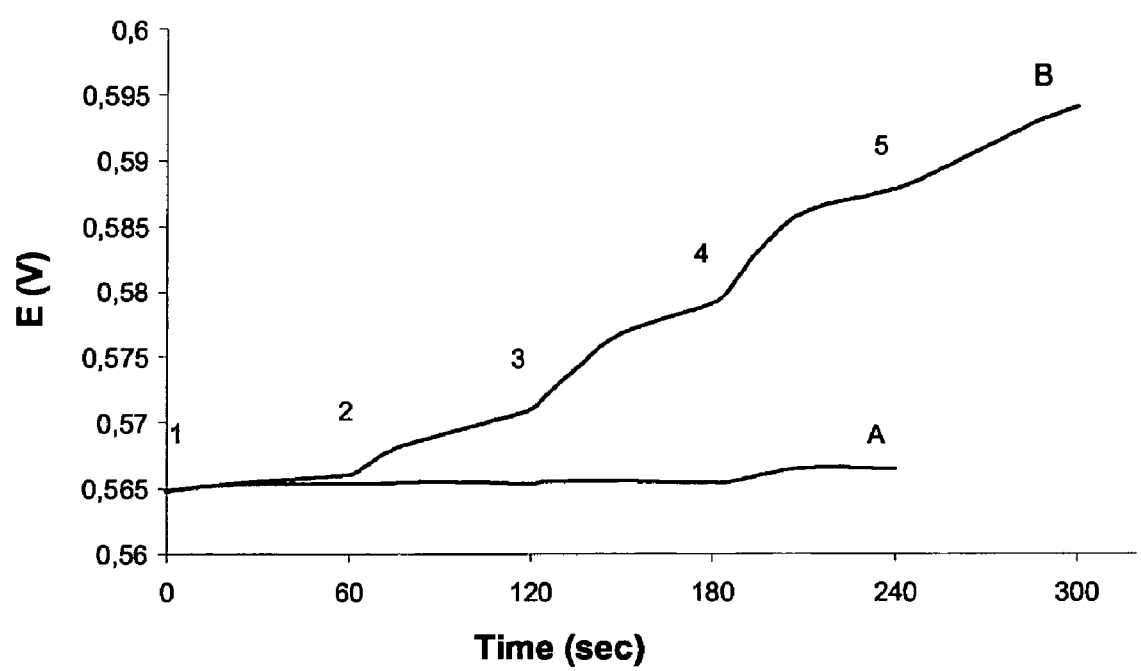

FIG. 21 shows the Potentiometric measurement of a platinum electrode where rabbit antibodies were immobilised on functionalised aniline by succinimidyl group. Curve A: base line Pt/Pani/Pani-R/IgG/TemPA without substrate of the β-lactamase. Curve B: The release of protons starts with the addition of the substrate (benzylpenicillin) and the electrode potential increases proportionally with the quantity of substrate. Point 1, $2,6.10^{-4}$ M; point 2, $2,6.10^{-3}$ M; point 3, $2,6.10^{-2}$ M; point 4, $2,6.10^{-4}$ M; point 5, $5,2.10^{-1}$ M.

Figure 22:
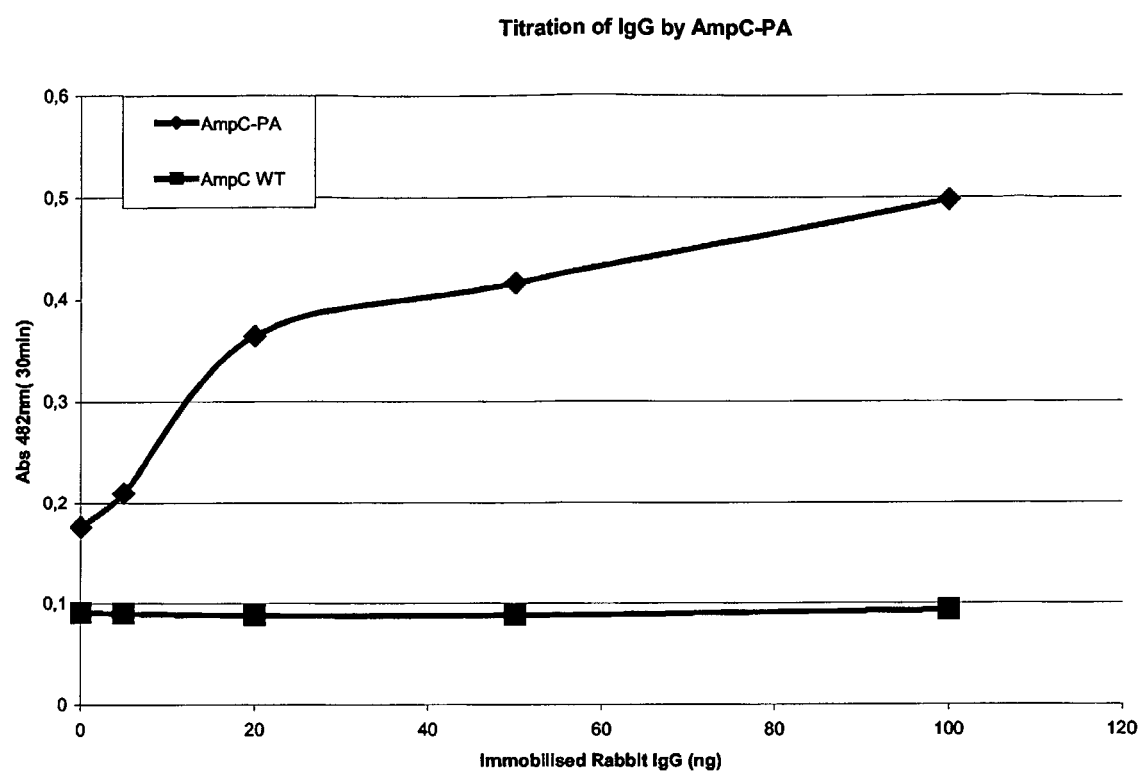

FIG. 22 shows the detection threshold between 5 and 100 ng of rabbit IgG binding to the Fc binding domain of *Staphylococcus aureus* protein A internalised into AmpC β-lactamase according to example 18.

Figure 23:
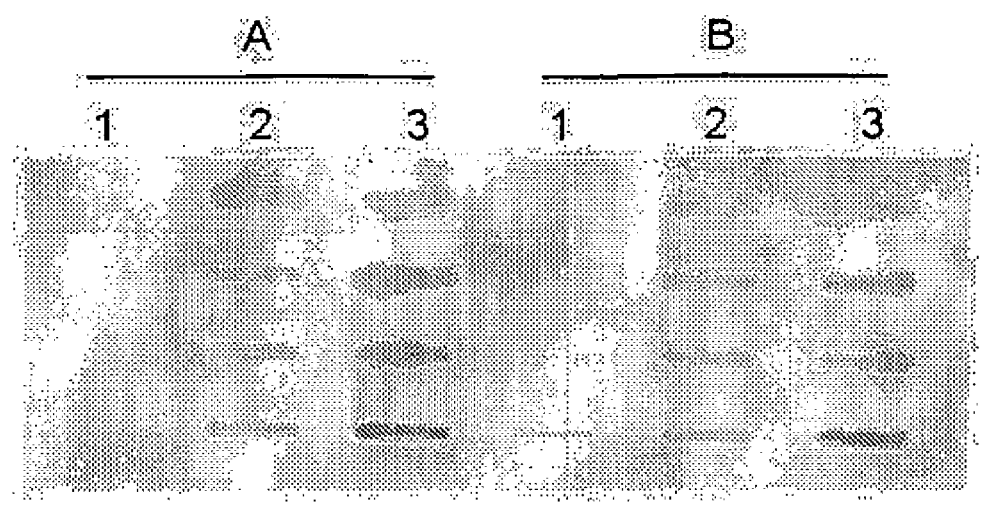

FIG. 23 shows binding of fluorescent β-lactam and antibody Fc-domain according to example 20. The BlaR-CTD_F514-PA of example 20 was acylated or not by fluorescent ampicillin and subsequently immobilized on a membrane. After saturation with non-fat dried milk 3%, Donkey anti-rabbit IgG coupled to horseradish peroxidase (Amersham Bioscience) were added. After washing and addition of ECL Immunodetection reagent (Amersham Bioscience) the slot-blot was revealed after 5 minutes. (A) represents non acylated and (B) represents acylated with Fluorescent ampicillin (B) BlaR-CTD_F514-PA;

lane 1: 0, 0.3, 0.6, 0.9 µg of total proteins;
lane 2: 1.2, 1.5, 1.8, 2.1 µg of total proteins;
lane 3: 2.4, 2.7, 3, 5 µg of total proteins.

DETAILED DESCRIPTION OF THE INVENTION

The technological advance offered by the present invention involves internalising the proteins or polypeptide fragments within the native structure of a carrier protein, an active-site serine β-lactamase. This new approach provides a means of replacing the internalised fragments in a 3-dimensional context close to the native situation. The constraints of the carrier protein imposed compel the internalised peptides to adopt a proper structure. This guarantees continuing biological activities in many cases. The outcome is the creation of a bifunctional hybrid protein. The hybrid β-lactamase according to the invention represents a single polypeptide. The use of this hybrid β-lactamase preferably is to study the interaction of the internalised homologous sequence with other separate molecules (for example antibodies) or to use this interaction of the internalised homologous sequence with other separate molecules in assays, either as binding interaction to be measured or as part of the test.

As mentioned above the hybrid β-lactamase according to the present invention is a single polypeptide. According to the present invention this single polypeptide excerts two biological functions: the first function is derived from the β-lactamase carrier as used. The second function is associated with the heterologous sequence. As a consequence the hybrid β-lactamase according to the invention combines the function of its basic constituents in one single peptide: the one function is that of the β-lactamase carrier and the other function is that of the heterologous sequence.

β-lactamase enzymes are divided into four classes. Classes A, C and D gather together the active serine enzyme. The fold of these three classes share a very close structure which is characterized by two domains. An α helix domain and a domain containing α helices and β sheets (see FIG. 1). In contrast class B β-lactamase are metallo-β-lactamases which need zinc ions to catalyse the β-lactam hydrolysis. The 3-dimensional structure of these class B enzymes has no common structure compared to the three other β-lactamases of class A, C and D.

The inventors constructed several hybrid proteins by inserting restriction sites in the DNA sequences of the β-lactamase in TEM-1 (*E. coli*), BlaL (*Streptomyces cacaoi*) and BlaP (*Bacillus licheniformis*) (class A). Once hybrid proteins on the basis of TEM-1, BlaL, BlaP have been successfully constructed further experiments with enzymes of other classes have been performed. Based on the structure of AmpC and by random insertions in BlaR-CTD, the restriction sites were inserted in a region common to the class A β-lactamase BlaP so as to be able to retain β-lactamase activity after insertion of large exogenous sequences. By that hybrid proteins based on AmpC from *E. coli* K12 (class C) and in BlaR-CTD from *Bacillus licheniformis* (class D), respectively, have also been constructed.

The inventors internalised exogenous nucleotide sequences in these genes. The hybrid genes produced during these operations provide a means of producing various bifunctional proteins.

The catalytic efficiency and the plasticity of the class A, C and D β-lactamases means they are effective candidates for constructing bifunctional proteins as a result of inserting sequences of exogenous peptides within the enzyme structure.

Figure 1:
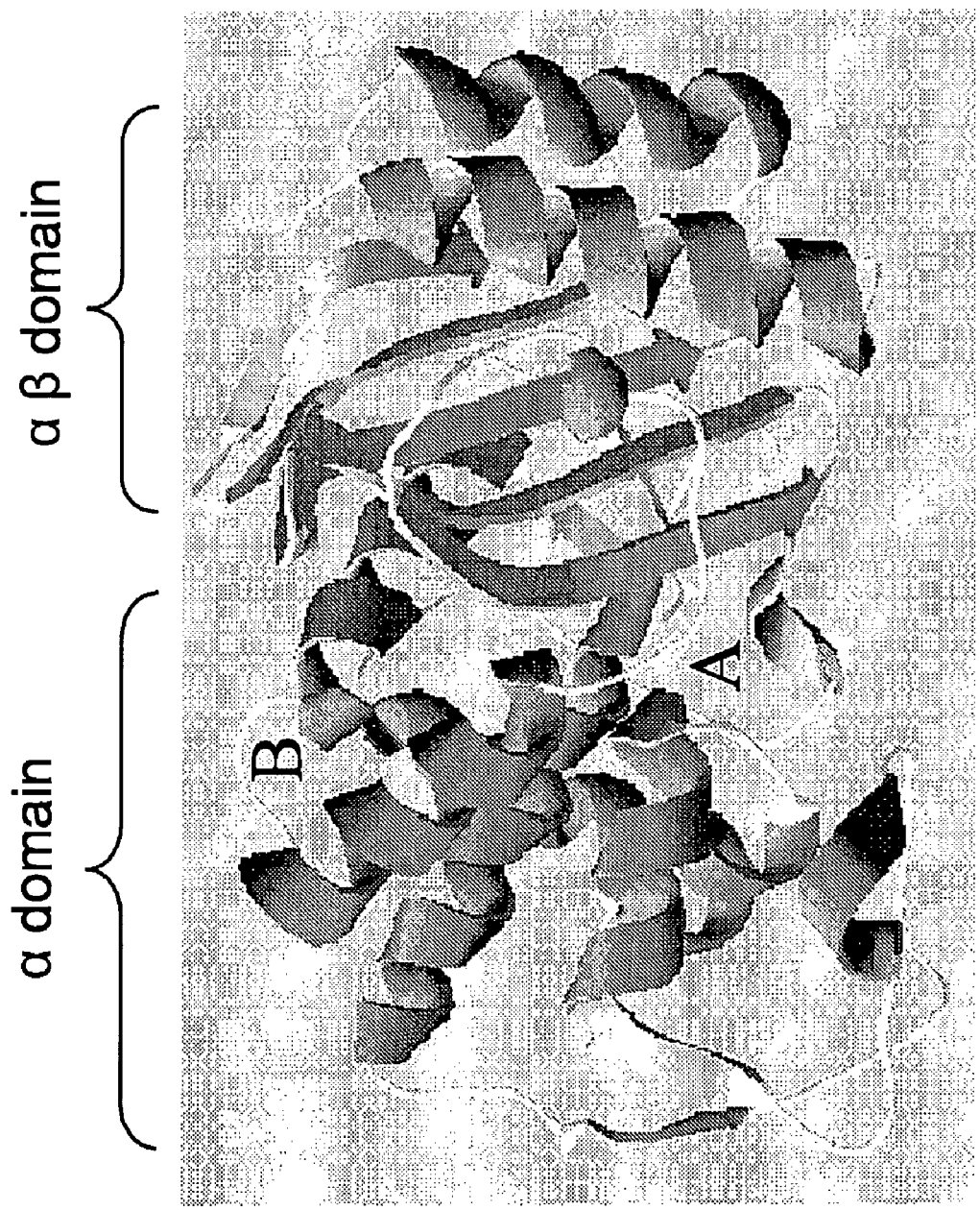

The TEM-1 β-lactamase is an active class A serine enzyme involved in the bacterial resistance to β-lactam based antibiotics, such as penicillin and cephalosporins. The mature form of the TEM-β-lactamase is a monomeric protein with 263 amino acids. Its 3D structure is hallmarked by two areas one of which is helice-rich and the other comprises α helices and β sheets (FIG. 1).

Figure 2:
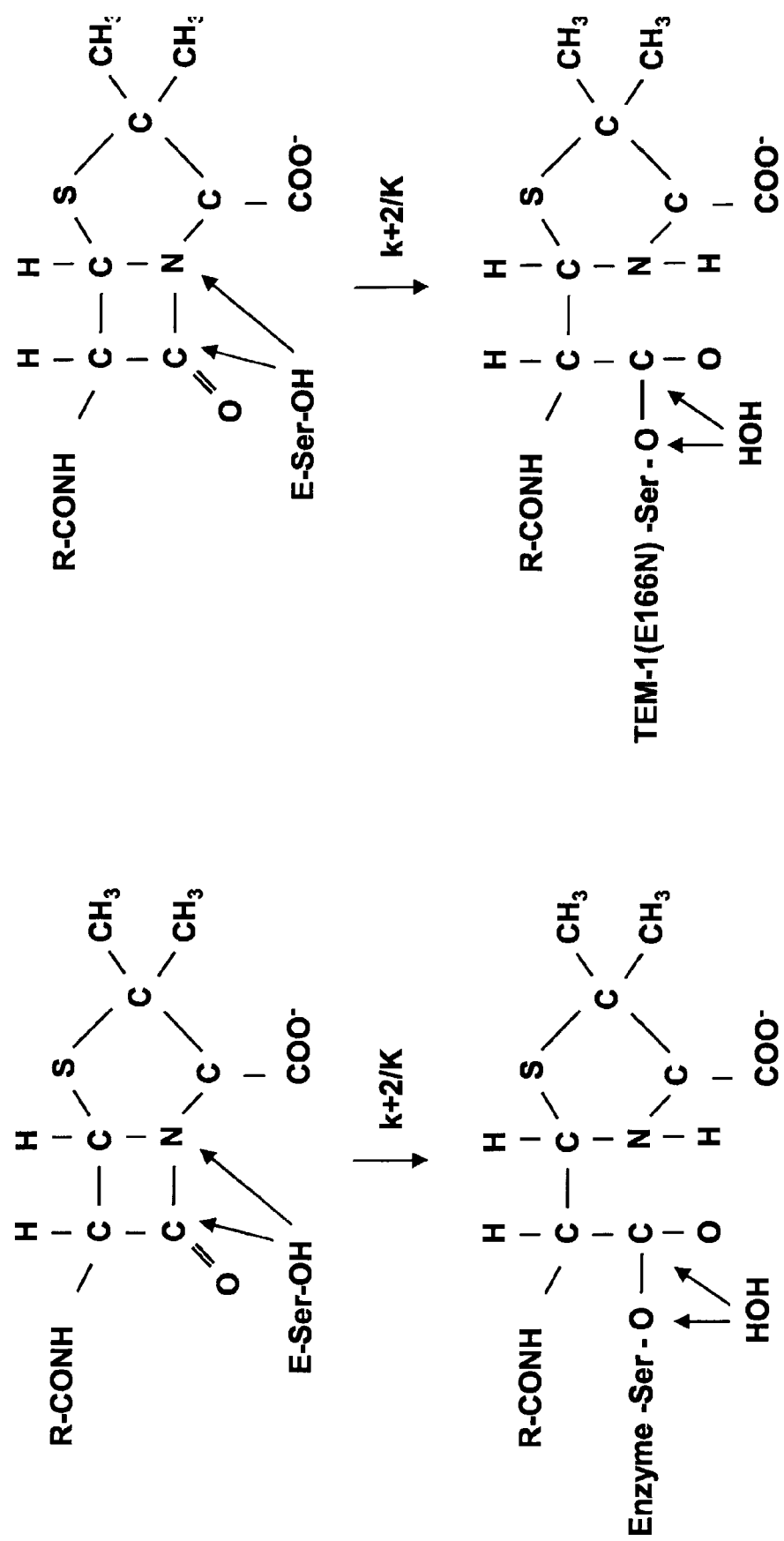
Figure 6:
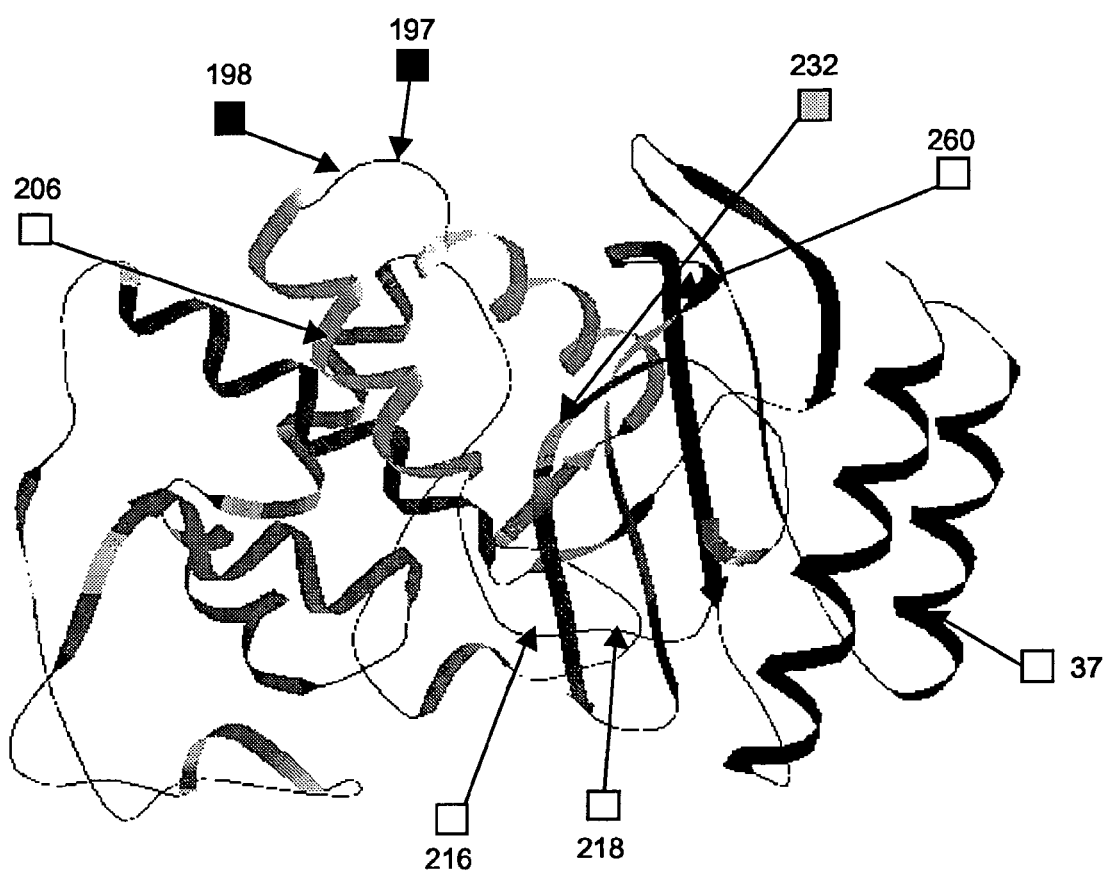
FIG. 6 shows the fold of the TEM-1 β-lactamase. The position of the permissive sites (filled square), the semi-permissive site (open square) and the non-permissive sites (grey square) are indicated.

The class A β-lactamases interact with the β-lactam based antibiotics to form an intermediate called acyl-enzyme where the antibiotic is covalently linked to the serine of the enzyme's active site (FIG. 2). The β-lactamases efficiently catalyse the deacylation stage (k3). This regenerates the active enzyme and releases a biologically inactive substance, where the amide linkage of the β-lactam of the antibiotic's nucleus is hydrolysed. In the case of the TEM-1 β-lactamase mutagenesis, experiments have shown that the deacylation reaction could be inhibited to produce a stable acyl-enzyme complex by replacing the glutamate 166 residues in asparagine (6) (FIG. 2). This feature permits the immobilisation of TEM-1 β-lactamase hybrid protein on β-lactam coated matrix.

As a result of the specificity, catalytic efficiency and plasticity of the TEM-1 β-lactamase, this protein is a valuable enzyme for developing new processes for detecting, assaying and orienting peptides and proteins used for therapeutic purposes. Towards this end, chromogenic and fluorescents substrates, suicide inhibitors and prodrug cytoxic agents have been developed.

Transposition and phage display experiments have shown the possibility of introducing or degenerating very short sequences of nucleotides (8 to 30 nucleotides) in the coding sequence for the TEM-1 β-lactamase and using these mutated genes as a basis for synthesizing a constantly functional enzyme (3, 5, 14, 15). In the context of this technology (WO98/23731) phage libraries ($10^{10}$ phages) bearing chimeras of the TEM-1 β-lactamase, where small degenerated peptides have been inserted, are used to select the degenerated peptide that has an affinity for a given target. This is a cumbersome, painstaking and evolutionary method, as it is not common for a peptide having a high affinity for the target to be selected. This characteristic involves creating several mutagenesis stages in respect of the peptide and the carrier protein so as to optimise the affinity of the hybrid protein. Hence this entails creating new banks and producing new screenings.

The idea of the present invention is not to create a chimera bank that theoretically covers all types of biodiversity but favours the insertion of large peptidic sequences present in proteins whose biochemical characteristics have already been clearly identified. Consequently, the present invention provides a means of internalising a peptidic sequence that has already been naturally optimised for a given property and averting (as is the case with the phage display technique) evolutionary mutagenesis reactions within the insert and carrier protein. With this system, the chimera banks may be restricted to a few thousand clones (or a few dozens) so the screening is quicker and more targeted.

Unlike the results obtained with the various TEM-1 β-lactamase utilisation methods, wherein the insertion site leads to a change in the TEM-1 enzymatic properties, this present invention marks a new departure because the inventors succeeded in identifying and creating, in a loop diametrically opposed to the active enzyme site (FIG. 1, site B: region Thr195 to Leu199), a region that is particularly favourable for internalising large exogenous sequences of peptides with a length preferably 11 or more amino acids. In this application this loop Thr195 to Leu199 is also referred to as the region forming the juncture between alpha helix 8 and alpha helix 9 of the TEM-1 β-lactamase and homologous enzymes which have a homologous three-dimensional structure, for example like BlaP and BlaL. The present invention applies to hybrid β-lactamase proteins wherein the carrier is selected from β-lactamases of classes A, C and D. Consequently, the present invention refers to hybrid β-lactamases wherein the carrier is an active-site serine β-lactamase. According to the present invention the heterologous sequence to be internalised is a sequence different from β-lactamases or parts thereof.

The results show that the polypeptides internalised in the context of the above identified loop are able to adopt a folding close to their native conformation, as their biological activity is retained. This specific feature offers new prospects for constructing and using new generations of hybrid bifunctional proteins where a specific and effective enzymatic activity is associated with the biochemical properties of another protein or a fragment of a protein. This special feature is the second focal point of this invention, as it is of crucial importance for developing the diagnosis test or the chromatography affinity system, because the β-lactamase activity is used to quantify the protein-macromolecule interaction or to immobilise the hybrid protein in an oriented way.

As described in the patent application WO 98/23731 the TEM-1 enzyme was shown to be sensitive to the action of proteases during production in bacterial system, which reduces the output of hybrid proteins. By applying the technology according to the present invention also to β-lactamases that are more resistant to proteases (BlaP and BlaL) further advantageous constructs have been provided. These BlaP and BlaL β-lactamases are produced by Gram positive organisms for which suitable production tools exist. Furthermore, these bacteria are well-known in industry and enjoy GRAS (Generally Regarded As Save) status. In the case of BlaP and BlaL is was possible to show that polypeptide insertion technique could be transferred to other β-lactamases of the same class and make a generally well-know improvement to the technology via the properties specific to these enzymes. The inventors also proved that the technique can be applied to β-lactamases of classes C and D.

In a further preferred embodiment the nucleotide sequence coding for the β-lactamase sequence is selected from:

a) nucleotide sequence coding for the β-lactamase TEM-1 (SEQ ID NO: 1; complementary strand);

b) nucleotide sequence coding for the β-lactamase BlaP (SEQ ID NO: 2);

c) nucleotide sequence coding for the β-lactamase BlaL (SEQ ID NO: 3);

d) nucleotide sequence coding for the β-lactamase AmpC (SEQ ID NO: 39);

e) nucleotide sequence coding for the β-lactamase BlaR-CTD (SEQ ID NO: 41);

f) nucleotide sequences which hybridise under stringent conditions to the nucleotide sequences of any one of a) to e) or fragments thereof. It should be noted that the nucleotide sequence SEQ ID NO: 1 given for the β-lactamase TEM-1 here is the complementary strand.

In a further preferred embodiment the heterologous sequence is partially of fully replacing the region between alpha helix 8 and alpha helix 9 or the region between alpha helix 9 and alpha helix 10. As described above the numbering of the helices refers to the TEM-1 β-lactamase. The present invention also includes homologous β-lactamases of class A, so that the identification of helix 8 and helix 9 in those homologous enzymes has to be applied in a corresponding manner. In case of the TEM-1 β-lactamase this region is defined by the amino acid residues Thr195-Leu199. The present invention further relates to β-lactamases of classes C and D which correspond to class A β-lactamases in respect to the three-dimensional structure. Therefore, in all active-site serine β-lactamases there can be identified helices which correspond to helix 8 and helix 9 of TEM-1 β-lactamase.

In a further preferred embodiment the heterologous sequence has a length of 11 or more amino acid residues, preferably in the range of 11 to 5000 amino acid residues, more preferably in the range of 11 to 3000 amino acid residues, more preferred in the range of 11 to 2000 amino acid residues, and further preferred in the range of 11 to 1000, even more preferred in the range of 11 to 300, and most preferred in the range of 18 to 200 amino acid residues. According to the present invention the insertion site within the β-lactamase class A, C or D for the heterologous sequence is determined in that way that any sequence of any length can be inserted essentially without disturbing the three-dimensional structure and the activity of the β-lactamase (also the so called "carrier protein"), as shown below.

In an alternative embodiment the heterologous sequence has a length of 18 or more amino acid residues, preferably in the range of 18 to 5000 amino acid residues, more preferably in the range of 18 to 3000 amino acid residues, more preferred in the range of 18 to 2000 amino acid residues, further preferred in the range of 18 to 1000, even more preferred in the range of 18 to 300, most preferred in the range of 18 to 200 amino acid residues.

In a further alternative embodiment the heterologous sequence has a length of 25 or more amino acid residues, preferably in the range of 25 to 5000 amino acid residues, more preferably in the range of 25 to 3000 amino acid residues, more preferred in the range of 25 to 2000 amino acid residues, further preferred in the range of 25 to 1000, even more preferred in the range of 25 to 300, most preferred in the range of 25 to 200 amino acid residues.

In yet another alternative embodiment the heterologous sequence has a length of 50 or more amino acid residues, preferably in the range of 50 to 5000 amino acid residues, more preferably in the range of 50 to 3000 amino acid residues, more preferred in the range of 50 to 2000 amino acid residues, further preferred in the range of 50 to 1000, even more preferred in the range of 50 to 300, most preferred in the range of 50 to 200 amino acid residues.

In still another alternative embodiment the heterologous sequence has a length of 18 or more amino acid residues, preferably in the range of 100 to 5000 amino acid residues, more preferably in the range of 100 to 3000 amino acid residues, more preferred in the range of 100 to 2000 amino acid residues, further preferred in the range of 100 to 1000, even more preferred in the range of 100 to 300, most preferred in the range of 100 to 200 amino acid residues.

According to the present invention the hybrid β-lactamase is a bifunctional protein. Since the carrier protein, the β-lactamase moiety of the hybrid β-lactamase retains its activity and also the heterologous sequence originally also has a kind of function (for example as an epitope) the hybrid β-lactamase possesses two functions and therefore is a bifunctional protein.

The heterologous sequence is related to a function on the level of the peptide/polypeptide. According to the invention the function of the heterologous sequence does not refer to its mere physical presence. In the sense of the invention the heterologous (peptide/protein) sequence does not have only a mere structural function but goes beyond that. The term "function" or "biological function" of the heterologous sequence as used herein means that the inserted heterologous peptide or polypeptide is able to specifically interact with or recognize other substances or compounds, for example a substrate or for example a biological macromolecule, for example by way of an epitope—antibody interaction. The interaction or recognition excerted by the heterologous sequence preferably refers to a molecule different from the hybrid β-lactamase itself or parts thereof. Consequently, the function of the heterologous sequence preferably involves specific interaction with other molecules (either low molecular compounds or macromolecules, for example biological macromolecules, for example peptides, proteins, nucleic acids). In particularly preferred embodiments the function of the heterologous sequence as such is selected from: being an epitope, being a specific binding partner for antibodies, being specially recognised and bound by antibodies, having a binding affinity to earth alkaline ions and metal ions, having enzymatic activity, being a toxin (for example STa heat-stable enterotoxin of E. coli), bearing a glycosylation site, bearing a glycosylated peptide, being a specific binding partner for any polypeptide or any ligand, having a binding affinity to dsDNA and ssDNA or RNA (having a binding affinity to nucleotide and polynucleotide).

Furthermore, it is particularly preferred that the heterologous sequence is selected from the group: STa (heat stable enterotoxin of Escherichia coli, SEQ ID NO: 21), protein A of Staphylococcus aureus, (SEQ ID NO: 23 and 25), protein G of Streptococcus pyogenes, (SEQ ID NO: 27 and 29), a linear antigenic determinant of the hemagglutinin of the Influenca virus (SEQ ID NO: 31), a fragment of human phospholipase—type II (hPLA$_2$) (SEQ ID NO: 33), LPS binding amino acid sequence (SEQ ID NO: 35), and nucleotide sequences which hybridise under stringent conditions to said nucleotide sequences or fragments thereof.

Furthermore the present invention provides a recombinant polypeptide which is encoded by the recombinant nucleotide sequence as described before.

The present invention therefore provides a recombinant polypeptide comprising at least a part of a bifunctional hybrid active-site serine β-lactamase protein, wherein the β-lactamase protein is bearing at least one heterologous sequence, wherein the hybrid protein is having two functions, the first function is associated with the β-lactamase portion and the second function is associated with the heterologous sequence having a biological function which is different from the first function.

Preferably, the β-lactamase protein is having conserved amino acid elements 1, 2 and 3, wherein element 1 is having the amino acid sequence SXXK, element 2 is having the amino acid sequence SDN in class A proteins, YXN in class C proteins, SX[V or T or N] in class D proteins, wherein the elements of classes A, C and D correspond to each other, and element 3 is having the amino acid sequence K[T or S]G, wherein the β-lactamase protein is bearing at least one heterologous sequence between element 2 and element 3.

In a preferred embodiment the β-lactamase protein is bearing at least one heterologous sequence in a region located between two neighboring alpha helices of the β-lactamase sequence, wherein the region is forming a juncture between the alpha helices of active-site serine β-lactamases, wherein said alpha helices correspond to the last two alpha helices before the alpha/beta domain.

In yet another embodiment the β-lactamase protein is bearing at least one heterologous sequence in a region located between two neighboring alpha helices of the β-lactamase sequence, wherein the region is selected from:

a) the region forming a juncture between alpha helix 8 and alpha helix 9 of TEM-1 β-lactamase;

b) the region forming a juncture between the alpha helices which are homologous to alpha helix 8 and alpha helix 9 of TEM-1 β-lactamase.

In a further embodiment the β-lactamase moiety is selected from the group:
  a) class A β-lactamase,
  b) class C β-lactamase,
  c) class D β-lactamase,
  d) a recombinant sequence of one or more of a) to c).

In one alternative the β-lactamase moiety is derived from class A β-lactamase, wherein β-lactamase class A protein is bearing the heterologous sequence in the region forming a juncture between alpha helix 8 and alpha helix 9.

Preferably the region forming a juncture between alpha helix 8 and alpha helix 9 is selected from the group:
  a) the amino acid sequence Thr195 to Leu199 of the TEM-1 β-lactamase;
  b) the amino acid sequence corresponding to the amino acid sequence Thr195 to Leu199 in TEM-1 β-lactamase.

In another alternative the β-lactamase moiety is derived from class C β-lactamase, wherein β-lactamase class C protein is bearing the heterologous sequence in the region forming a juncture between alpha helices, which correspond to alpha helix 8 and alpha helix 9 in TEM-1 β-lactamase.

Preferably, the region forming a juncture is selected from the group:
  a) the amino acid sequence K239 to E245 of the AmpC β-lactamase;
  b) the amino acid sequence corresponding to the amino acid sequence K239 to E245 of the AmpC β-lactamase.

In yet another embodiment the β-lactamase moiety is derived from class D β-lactamase, wherein β-lactamase class D protein is bearing the heterologous sequence in the region forming a juncture between alpha helices, which correspond to alpha helix 8 and alpha helix 9 in TEM-1 Gβ-lactamase.

Preferably, the region forming a juncture is selected from the group:
  a) the amino acid sequence N510 to Q516 of the BlaR-CTD β-lactamase;
  b) the amino acid sequence corresponding to the amino acid sequence N510 to Q516 of the BlaR-CTD β-lactamase.

Furthermore the present invention provides a recombinant polypeptide which is encoded by the recombinant nucleotide sequence as described before. The present invention therefore provides a recombinant polypeptide comprising at least a part of a bifunctional hybrid β-lactamase class A protein, wherein that the β-lactamase class A protein is bearing at least one heterologous sequence in a region located between two neighboring alpha helices of the β-lactamase sequence, wherein the region is selected from:

a) the region forming a juncture between alpha helix 8 and alpha helix 9 of the TEM-1 β-lactamase;

b) the region forming a juncture between the alpha helices, which correspond to the alpha helix 8 and alpha helix 9 of the TEM-1 β-lactamase.

The further preferred embodiments of the recombinant polypeptides are outlined in respect to the description of the respective nucleotide sequence encoding the hybrid β-lactamase.

Furthermore, the present invention provides the use of the recombinant nucleotide sequence of the recombinant polypeptide for vaccination. As described above the enterotoxin of Escherichia coli (STa) as such is not immunogenic. However, by incorporating this peptide into a β-lactamase class A protein, namely in a region on the surface of this carrier protein, the possibility is given to raise antibodies against the heterologous sequence (STa), as shown below. Therefore, it is also preferred to use the recombinant nucleotide sequence or the recombinant polypeptide of the present invention for raising antibodies against the heterologous sequence. A further preferred embodiment is the use of the same for epitope mapping for a different protein or polypeptide. For epitope mapping smaller peptides having for example a length of 5 to 30 amino acid residues which are covering the polypeptide to be examined are used for being introduced as heterologous sequence in the region forming a juncture between alpha helix 8 and alpha helix 9 of the TEM-1 β-lactamase or homologs thereof. As result a set of hybrid β-lactamase class A protein is constructed bearing (overlapping) sequences as heterologous sequence of the polypeptide to be examined. This set of hybrid β-lactamases differing within the homolgous sequence is then used for studying the epitopes of the polypeptide in question can be studied.

The present invention also provides the use of the recombinant nucleotide sequence or the recombinant polypeptide of the present invention for affinity chromatography, particularly for the concentration and/or purification of antibodies directed against the heterologous sequence of the hybrid β-lactamase. By using a mutant of the β-lactamase class A protein (glutamate 166 asparagine) the β-lactamase can be immobilised on a matrix which is coated with the substrate (β-lactam). Since the hybrid β-lactamase is presenting the heterologous sequence on its surface it is possible to concentrate and/or purify antibodies which are directed against this heterologous sequence, which is immobilised on for example a column via the β-lactamase carrier protein, which is linked to its substrate on the matrix of the column.

In a similar way it is possible to detect molecules which are binding to the heterologous sequence qualitatively and/or quantitatively. It is particularly preferred that the molecules binding to the heterologous sequence are antibodies or antibody fragments, polypeptides, dsDNA, ssDNA, RNA or small ligands. The method which may apply for the qualitative and/or quantitative detection is well known as ELISA.

Furthermore the recombinant polypeptide preferably may be used in molecular diagnostics. For example, the protein A of *Staphylococcus aureus* or protein G of *Streptococcus pyogenes* of fragments thereof may be used as heterologous sequence incorporated into β-lactamase A protein. This heterologous sequence is exposed on the surface of the carrier protein (β-lactamase class A) and binds to the Fc region of antibodies. By using substrates of the β-lactamase which upon cleavage show a colour change, this system can be applied for the quantitative and/or qualitative detection of antigens to which the antibody is directed.

The present invention also provides a pharmaceutical composition comprising a recombinant polypeptide. For example a recombinant polypeptide of the present invention may be used for drug-targeting. The homologous sequence which is incorporated into the hybrid β-lactamase protein may be specifically selected from those determinants which are bound by cellular receptors (for example of cancerous cells or cells infected by a virus). Preferably a (therapeutically) inactive pro-drug is used, which is activated through cleavage by the β-lactamase moiety into an active drug. Then such cellular targets which are involved in a disease can be inhibited or destroyed. The present invention also provides the use of a recombinant polypeptide for the manufacture of a medicament for the preventive and/or therapeutic treatment of diseases selected from the group cancer, viral diseases and bacterial diseases (or infection diseases), autoimmune diseases and allergy.

The present invention also provides a method for screening a compound for treatment, prevention and/or diagnosis of a disease which comprises the step of detecting the interaction between the homologous sequence of the hybrid β-lactamase according to the present invention and a protein or polypeptide which binds to the homologous sequence in the presence of a compound to be tested. Preferably the compound to be tested is selected as the candidate of an effective medicament wherein the compound has an effect on the interaction between the homologous sequence inserted into the hybrid β-lactamase and the peptide which binds to the homologous sequence.

In a particularly preferred embodiment the method comprises the steps of:

a) subjecting the recombinant polypeptide of the present invention and a polypeptide which binds to the homologous sequence to interaction with each other in the presence of the compound to be tested:

b) subjecting the recombinant polypeptide of the present invention and a polypeptide which binds to the homologous sequence to interaction with each other in the absence of the compound to be tested;

c) detecting the interactions in the steps a) and b), and d) comparing the interactions in the steps a) and b) to chose the compound having an effect on the interaction as a candidate of an effective medicament.

The present invention further provides a biological sensor comprising a recombinant polypeptide of the present invention. The term biosensor has been applied to devices either (1) used to monitor living systems, or (2) incorporate biologic or biomimetic elements. The consensus, however, is that the term should be reserved for use in the context of a sensor incorporating a biological element such as an enzyme, antibody, nucleic acid, microorganism or cell. The term "biosensor" as used in this patent application will be defined as:

analytical devices incorporating a biological material or a biomimetic material (e.g. tissue, microorganisms, organelles, cell receptors, enzymes, antibodies, nucleic acids etc.), intimately associated with or integrated within a physicochemical transducer or transducing (micro)system, which may be optical, electrochemical, thermometric, piezoelectric or magnetic.

The usual aim of a biosensor is to produce either discrete or continuous digital electronic signals which are proportional to a single analyte or a related group of analytes.

In a preferred embodiment antibodies are immobilised on a conductive polymeric material. The hybrid protein carrying as homologous sequence an epitope which is specifically recognized and bound by the antibody is used for detecting the respective antibody. Upon cleavage of the substrate by the β-lactamase moiety protons will be generated which can be detected by potentimetric measurement. In an alternative embodiment the antigen is immobilised on the conductive polymeric material. By the use of a hybrid β-lactamase class A protein, wherein the heterologous sequence is binding to the Fc region of antibodies, the presence of antibodies directed to the immobilised antigen can be measured upon cleavage of the substrate and the generation of protons which again are detected by potentiometric measurement.

In a bid to validate the various fields of application, several hybrid proteins were constructed by inserting restriction sites in the DNA sequences of the TEM-1 β-lactamases, BlaP and BlaL. Belonging to the class A group of β-lactamases, these enzymes originate from *Salmonella thyphimurium*, *Bacillus licheniformis* and *Streptomyces cacaoi* respectively. The restriction sites were inserted in a region common to class A β-lactamases, so as to be able to retain β-lactamase activity after large exogenous sequences have been internalised.

Various exogenous nucleotide sequences were internalised in these recombinant genes. The hybrid genes produced during these operations provide a means of producing various bifunctional proteins, for example:

1. A hybrid protein of the TEM-1 β-lactamase where the STa heat stable enterotoxin protein of *Escherichia coli* is internalised (TEMSTA).
2. Hybrid proteins of the TEM-1 β-lactamase where 1 to 3 repeated domains of the *Staphylococcus aureus* protein A are internalised (TEM-PA).
3. Hybrid proteins of the BlaP β-lactamase where 1 to 3 repeated domains of the *Staphylococcus aureus* protein A are internalised (BlaP-PA).
4. Hybrid proteins of the TEM-1 β-lactamase where the domain/domains B1 and/or B2 of the protein G of *Streptococcus pyogenes* are internalised (TEM-PG).
5. Hybrid proteins of the BlaP β-lactamase where the domain/domains B1 and/or B2 of the protein G of *Streptococcus pyogenes* are internalised (BlaP-PG).
6. A hybrid protein of the BlaP β-lactamase where a linear antigenic determinant of the hemagglutinin of the Influenza virus is internalised (BlaP-HA).
7. Hybrid proteins of the TEM-1 β-lactamase where fragments of human phospholipase—type II, hPLA$_2$ are internalised (TEM-PLA2).
8. A hybrid protein of the BlaP β-lactamase where fragments of multimerised polypeptides comprising three amino acids repeated in tandem and presenting an affinity for bacterial endotoxins are internalised (BlaP-LPS).
9. A hybrid protein of the β-lactamase AmpC in which one Fc-binding domain of the *Staphylococcus aureus* protein A is internalised (AmpC-PA).
10. A hybrid protein of the β-lactamase BlaR-CTD in which a linear antigenic determinant of the Influenza virus hemagglutinin is internalised (BlaR-CTD-HA).
11. A hybrid proteins of the β-lactamase BlaR-CTD in which one Fc-binding domain of the *Staphylococcus aureus* protein A is internalised (CTD-PA).
12. Use of the hybrid protein BlaP-PA in an electrobiochemical biosensor system.

EXAMPLES

Methodology for Constructing Hybrid Proteins

Example 1

Inserting Unique Restriction Sites in the Genes of the TEM-1, BlaP and BlaL β-Lactamases so as to Internalise Exogenous Nucleotide Sequences The coding sequence of the β-lactamase TEM-1 which was used for internalising exogenous sequences of peptide initially contains a KpnI restriction site. In order to broaden the range of DNA fragments to be internalised in the carrier protein, two types of restriction cassettes were inserted into the KpnI site (FIG. 3). Among the new restriction sites, the SmaI site produces blunt ends compatible with all nucleotide fragments also having blunt ends. This change provides a means of making out the internalisation of the random nucleotide fragments originating with a gene of interest or the genomic DNA of any organism. *E. coli* production assays have shown that the new TEM-1 hybrid proteins retain their β-lactamase activity after the restriction cassettes have been internalised.

As FIG. 4 shows, the 3D structure of the BlaP β-lactamase of *B. licheniformis* is very close to that of TEM-1. This specific feature is shared by all β-lactamases of the same class. Owing to their insensitivity to the proteases action, a SmaI restriction site was inserted into the BlaP and BlaL coding sequences to allow exogenous nucleotide sequences to be internalised (FIG. 5). The restriction site was inserted in a region that was the same as the one used to internalise exogenous peptides in TEM-1 (FIG. 5). By the end of this process, is was possible to show that BlaP and BlaL β-lactamases retained their enzymatic activity.

Example 2

Synthesis of Hybrid Proteins TEM-1 and the Thermostable Enterotoxin STa of *Escherichia coli* (TEM-STA)

STa is a thermostable toxin mainly produced by enterotoxic *Escherichia coli* (*E. coli*) strains found either in animal as bovine or in human. STa induces severe and lethal diarrhoea in human and new borne calf respectively (Mainil J, 2000). The thermostable enterotoxin STa is a polypeptide of 18 amino acid residues. It exhibits a discrete three-dimensional structure, which is stabilised by the presence of three disulfide bonds (Gariepy et al, 1986; Shimoniski et al, 1987). The native fold of the polypeptide only mediates the toxicity.

The small size of STa does not allow its recognition by the host immune system and no anti-STa antibodies can be produced. Therefore, no protection of the host and no vertical protection (mother-foetus) are possible.

In order to develop an immune response against STa, the 18 residues can be linked to a large protein (called the carrier protein). The aim is to design a set of hybrid protein in which the STa peptide will be inserted into the TEM-1 class A β-lactamase scaffold. The different hybrid proteins will be produced in *E. coli* and purified to homogeneity. The different proteins will be injected in mice and the immune response toward the carrier protein and the insert will be studied.

Results

Example 3

Selection of Permissive Sites

When performing the present invention the STa amino acid sequence was introduced into eight different positions of TEM-1. Namely, STa was placed after amino acid residues 37, 197, 198, 206, 216, 218, 232 and 260 of TEM-1 respectively (FIG. 6).

Those hybrid proteins were obtained by introducing the DNA coding sequence for the 18 amino acid peptide STa into the gene ampR of pBr322. The different hybrid proteins were produced in *E. coli*. The production of a stable and active enzyme was tested as follow:

a) Western blot with anti-TEM antibodies were performed to verify the production of the hybrid.

b) Determination of the MIC (minimal inhibitory concentration) of ampicillin for the different *E. coli* strains.

These data indicated that three different types of insertion sites could be defined. The sites in position 197, 198, 216 and 218 are permissive (detection of TEM by western blot and high MIC values). The sites in position 37, 206 and 260 are semi permissive (detection of TEM by western blot and low MIC values). The site in position 232 is a non-permissive site (no TEM-1 production and low MIC). Two positions were selected: The first one is the position 197, which is located on solvent exposed loop, and position 216 located on a buried loop.

Example 4

Production of the Different Hybrid Proteins

The hybrid proteins in which the STa sequence was inserted in position 197 and 216 were produced in E. coli. Their corresponding genes were inserted in a pTAC11 vector. The hydrids TEM197STa and TEM216STa were produced at 18° C. in LG media. The enzymes were purified in three purification steps (one QFF sepharose pH 7.5, a QFF sepharose pH 6.5 and a superdex 75 molecular sieve). The purification yield was estimated at 2 mg/liter of culture for the two enzymes.

The TEM197H (TEM-1+amino acids inserted in position 197) was also produced in E. coli. The production was performed in a SB media. The culture was incubated at 18° C. for 28 h. The enzyme was purified as described above. The purification yield was 12.6 mg/liter of culture.

Finally, as protein control, the STa sequence was introduced at the C-terminal of the glutathion-5-transferase (GST). The fusion protein was purified by affinity chromatography. The purification yield was 30 mg/liter of culture.

Example 5

Biological Activity of TEM197 STa and TEM216STa

1) Beta-lactamase activity. Table 1 shows the steady state kinetic parameters for the different hybrid proteins and the wild type enzyme. The data indicated that the catalytic efficiencies of the different hybrids are lower that the WT. Nevertheless, it could be demonstrated that the insertion of the STa moiety does not drastically impaired the catalytic efficiency of the TEM-1 enzyme. The conclusion is that the fold of the TEM-1 is not strongly affected by the presence of STa.

2) Toxicity of the hybrid proteins. The toxicity of the hybrid proteins were tested by suckling mouse assay (Gianella et al, 1976). The toxicity of STa is due to the secretion of physiological fluid in the bladder. The mass of fluid can be estimated by the determination of the ratio between the weight of the bladder and the weight of the mouse carcasse (I/C). If I/C<0.075, no toxic effect is detected. If 0.075<I/C<0.083 represent an intermediary effect of the toxin while an I/C>0.083 indicated an strong toxic effect. Three control reactions were made by using a purified STa peptide, a supernatant of E. coli which produce (B44) or not the enterotoxin STa. The data presented in table 2 indicated that the TEM197STa and TEM216STa yielded a toxic activity.

Figure 7:
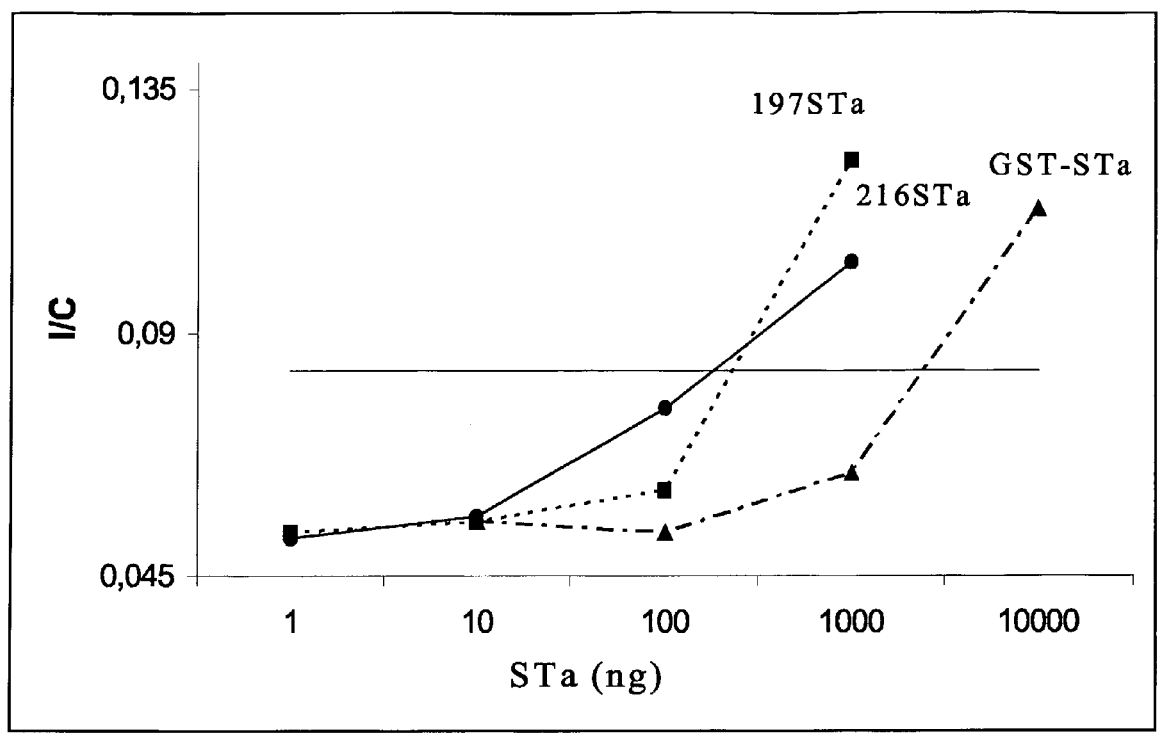
FIG. 7 shows the toxicity titration curve of the hybrid proteins.

3) Titration of the STa toxicity. The suckling mouse assay was performed for different protein concentrations of 197STa, 216STa and GST-STa. The I/C values were determined in function of the hybrid protein concentration (FIG. 7). These data indicated that the toxicity of the TEM197STa and TEM216STa were 200 fold lower than the native STa. Interestingly, the toxicity of the GST-STa was 2000 fold lower compared to STa.

Example 6

Immunization Assays

Six groups of three-month-old BALB/c (H-2d) female mice (Dr. Collard, Department of Animal immunology, Centre d'Economie Rurale) were used for immunisation with the different purified recombinant proteins. The mice were immunised with 50 μg of protein diluted in 50 mM sodium phosphate pH 7.2, 0.1 M NaCl (PBS buffer) containing the QuilA adjuvant (Spikoside, Isotech AB, Luleà, Sweden). Three, six weeks and 16 weeks later (day 21, 42 and 112 respectively), the mice were boosted with 50 μg of the same recombinant protein. At two weeks time intervals after the first injection (day 14) and after each boosts (day 35, 56 and 127), sera were collected, pooled per group of mice, and then tested for the presence of anti-TEM and anti-STa antibodies by ELISA (FIGS. 8 A and B). The presence of IgG anti-TEM was found in the serum collected at day 14 for TEM197STA and TEM216STa and at day 35 in the case of TEM197H respectively. In addition, the IgG anti-Sta were produced against TEM197STa, TEM216STa and GST-STa. The immune response was detected in all the case after the second boost. The production of antibodies was always higher when the GST-STa was injected into the mice.

Example 7

Titration Curve of Anti-Tem IgG Antibodies and Isotyping of the Immune Response

FIG. 9 shows that, after the second boost, the level of anti-TEM antibodies in the different serum (with the exception of GST-STa) was equivalent. The titre was estimated to be 10000.

The nature of the different antibodies produced against TEM-1 was characterized (FIG. 10). The nature of the antibodies (IgG1, IgG2, IgG2a, IgG2b, IgA and IgM) was determined by ELISA. The TEM-H was used for this experiment and the day 127—serum of mice immunised with TEM-H was chosen. The data indicated clearly that the immune response yielded t a strong production of IgG1 and IgG2 antibodies. The IgA and IgM antibodies were poorly expressed. In addition the IgG2 response was further characterised. Furthermore, also the IgG2a and IgG2b were found. These data indicated that the presence of TEM-1 can induced both the Th1 and Th2 immune response.

Example 8

Stability of the Immune Response Versus Time

The level of total anti-TEM IgG was measured by ELISA in serums collected at day 127 and 356 after the first injection. No boosts were realised after day 127. The results (FIG. 11) showed that the IgG level was always slightly higher in the serum day 356 compared to those collected at day 127. Consequently, the immune response is considered to be stable for at least one year after a contact between the mice and the TEM β-lactamase.

Example 9

Neutralization of the Native STa Toxicity

The native STa enterotoxin was incubated in presence of diluted (4 to 32 fold) serum containing the antibodies raised against GST-STa, TEM197STa and TEM260STa. The solutions were incubated for 16 hours at 4° C. The residual toxicity of the sample was estimated by "suckling mouse assay" (table 3).

The data indicated that the incubation of STa with the TEM197STa or GST-STa serum allowed a neutralisation of the biological activity of STa. Unfortunately, no clear data could be obtained for the TEM232STa.

TABLE 1

Kinetic parameters of the TEM197STa, TEM216STa, TEM197H and TEM-1

| Antibiotics | proteins | $k_{cat}$ ($S^{-1}$) | $K_M$ (μM) | $k_{cat}/K_M$ ($\mu M^{-1}s^{-1}$) |
|---|---|---|---|---|
| Benzylpenicillin | TEM-1 | 1500 | 18 | 80 |
| | 197H | 600 | 65 | 9 |
| | 197STa | 56 | DELAY | DELAY |
| | 216STa | 70 | DELAY | DELAY |
| Nitrocefin | WT | 930 | 52 | 18 |
| | 197H | 770 | 170 | 4.5 |
| | 197STa | >560 | >280 | 2 |
| | 216STa | N.D. | N.D. | N.D. |
| Cephaloridine | WT | 1500 | 670 | 2.2 |
| | 197H | >1000 | >1000 | 1 |
| | 197STa | 256 | 172 | 1.5 |
| | 216STa | 4.5 | 720 | 0.0062 |

TABLE 2

Determination of the toxicity of the different hybrid proteins.
Positive control: *E. coli* B44 producing STa
Negative control: *E. coli* non-producer of STa

| Proteins | (I/C) | Toxicity |
|---|---|---|
| 197H | 0.0545 ± 0.001 | − |
| 197STa | 0.107 ± 0.009 | + |
| 216STa | 0.106 ± 0.011 | + |
| GST-STa | 0.074 ± 0.006 | Int |
| *E. coli* B44 | 0.0925 ± 0.001 | + |
| *E. coli* | 0.0525 ± 0.001 | − |

TABLE 3

Neutralisation of the STa toxicity by the mice serum containing anti-GST-STa, TEM197STa, TEM260STa immuno-globulins. The toxicity of the serum TEM197STa, TEM197H and the serum collected at day 1 was tested by suckling mouse assay. The I/c ratio was measured with the serum diluted 8 fold. The toxicity of the protein samples TEM197STa and STa was also determined. The toxicity was measured by the I/C ratio. The STa peptide is diluted 16 fold in PBS buffer. The different serum were diluted 4 fold (4x), 8 fold (8x), 16 fold (16x) and 32 fold (32x) respectively. A positive and a negative sign indicate that the solution yielded or not a toxic response respectively.

| | Samples | STa | I/C | Toxicity |
|---|---|---|---|---|
| Controls | 197Sta | / | 0.102 | + |
| | / | STa | 0.093 | + |
| | Serum 197STa 8x | / | 0.059 | − |
| | Serum 197H 8x | STa | 0.073 | − |
| | Serum day1 | STa | 0.051 | − |

TABLE 3-continued

Neutralisation of the STa toxicity by the mice serum containing anti-GST-STa, TEM197STa, TEM260STa immuno-globulins. The toxicity of the serum TEM197STa, TEM197H and the serum collected at day 1 was tested by suckling mouse assay. The I/c ratio was measured with the serum diluted 8 fold. The toxicity of the protein samples TEM197STa and STa was also determined. The toxicity was measured by the I/C ratio. The STa peptide is diluted 16 fold in PBS buffer. The different serum were diluted 4 fold (4x), 8 fold (8x), 16 fold (16x) and 32 fold (32x) respectively. A positive and a negative sign indicate that the solution yielded or not a toxic response respectively.

| | Samples | STa | I/C | Toxicity |
|---|---|---|---|---|
| Serums | Serums | | | |
| | 4x GST-STa | STa | 0.060 | − |
| | 8x | STa | 0.075 | − |
| | 16x | STa | 0.091 | + |
| | 32x | STa | 0.084 | + |
| | 4x 197STa | STa | 0.063 | − |
| | 8x | STa | 0.082 | +/− |
| | 16x | STa | 0.088 | + |
| | 32x | STa | 0.094 | + |
| | 4x 216STa | STa | 0.120-0.054 | + − |
| | 16x | STa | 0.144-0.074 | + − |
| | 32x | STa 16x | 0.101-0.120 | + + |

CONCLUSIONS

The results indicates that:

1) The TEM-1 β-lactamase allowed the insertion of large peptide sequences between the helices α8 and α9 (position 197) and also between the helices α9 and α10 (site 216) without any major loss of activity and stability.
2) Different hybrid proteins (TEM197STa, TEM198STa, TEM216STa, TEM260STa, GST-STa and TEM197H respectively) were produced and purified to homogeneity.
3) The hybrid proteins TEM197STa and TEM216STa possess a rather high residual catalytic efficiency ($k_{cat}$/KM>2 $\mu M^{-1} s^{-1}$ for nitrocefin).
4) The different hybrid proteins exhibited a reduced toxicity compared to the native STa polypeptide.
5) Both Th1 and Th2 response toward the TEM enzyme but also against STa could be detected.
6) The serum raised against TEM197STa contains antibodies that allow a neutralisation of the biological activity of the native STa enterotoxin.

Example 10

Construction of Hybrid Proteins of the TEM-1 β-Lactamase where 1 to 3 Repeated Domains of the *Staphylococcus aureus* Protein A are Internalised (TEM-PA)

The aim was to internalise one or more repeated domains of protein A in position 197 of the TEM-1 β-lactamase (197/SmaI). Protein A is composed of 5 repeated domains (FIG. 12A). Each of the repeated domains of protein A is organised into three α helices (FIG. 12B) interacting with the CH2 and CH3 domains of the Fc part of the IgG. This link is primarily stabilised via hydrophobic interactions. FIG. 12 A, B, C.

In order to amplify the repeated domains of protein A, two primers (5'-TCAGTTAACAATTTCAACAAAGAACAA-CAAAATGCT-3', SEQ ID NO: 7; 5'-TCGAAATTTTTTGT-TGTCTTCCTCTTTTGG-3', SEQ ID NO: 8) were created which hybridise at the start and end of the gene encoding the proteins A's domain B. The high similarities between the nucleotide sequences of the 5 repeated domains of protein A allow the 5 domains to be amplified on the basis of the same set of primers. In the case of the more or less long polymerisation times, several repeated domains may be amplified via the same PCR fragment (FIG. 12C). The latter feature allows a bank of nucleotidic sequences to be obtained where the five repeated domains of protein A are coded separately or in association with each others. In order to provide a highest degree of freedom for the correct folding of the domain internalised in the β-lactamase and in a way that reduces the effect of its steric constraints on the carrier protein (TEM-1), two amino acid residues were added on either side of the fragment. Ser Val for the N-terminal part and Phe Arg for the C-terminal end. It is important to stress that these primers are designed so as to amplify a fragment that preserved the reading frame of TEM-1 and of the repeated domains of protein A during the internalisation reaction.

The structural gene of the protein A, originates from a *Staphylococcus aureus* strain isolated at the Centre for Protein Engineering, was amplified by PCR with the following primers: 5'-CATATGAAAAAGAAAAACATTTAT-TCAATTCGT-3' SEQ ID NO: 9; 5'-GGATCCTTATAGT-TCGCGACGACGTCCAGCTAA-3' SEQ ID NO: 10; and in the following conditions: 95° C.-180 sec, 95° C.-30 sec, 55° C.-60 sec, 72° C.-120 sec 30 cycles, mixture of Taq polymerase/Pfu polymerase and cloned into the pGEM-T-easy plasmid.

The repeated domains of protein A (180-pb) were amplified by PCR (95° C.-180 sec, 95° C.-30 sec, 60° C.-60 sec, 72° C.-60 sec 35 cycles; mixture of Taq polymerase/Pfu polymerase) on the entire gene. An analysis of the amplification product for the repeated domains of protein A shows a ladder profile where the size of the amplified fragments is a multiple of 180-pb (FIG. 12C). The PCR product was purified from an agarose gel, bunt ended by the action of the Pfu polymerase then dephosphorylated by Calf intestine phosphatase. The library of protein A PCR fragments was shotgun cloned in the TEM-1 β-lactamase gene that was cloned beforehand in the expression construct pROGENO-1 and digested by SmaI. The pROGENO-1 plasmid allows for a high constitutive expression of the recombinant β-lactamases in *E. coli*. In this plasmid, a unique restriction site recognised by the SmaI enzyme is present in position 197 of the TEM-1 β-lactamase. After transformation, the bacteria were selected via LB agar plate+Spectinomycin (100 µg/ml final) and cephaloridin (50 µg/ml). The cephaloridin is an antibiotic with a β-lactam ring hydrolysed by the TEM-1 wild-type and recombinant protein.

After plate selection, a colony PCR reaction analysis was performed to controlled the size of the TEM-1 gene. Towards this end, primers outcrossing upstream and downstream from the coding sequence of the mature form of TEM-1 (5'-cgg-gagctcaggctcacccagaaacgctggtg-3'; 5'-cgggaattctcaccaatgct-taatcagtgaggcacc (SEQ ID NO 11 and SEQ ID NO:12); 95° C.-180 sec; 95° C.-30 sec, 65° C.-60 sec, 72° C.-90 sec 35 cycles, mixture of Taq polymerase/pfu polymerase) were used. In a population of 30 clones, all of them were bigger than the encoding TEM-1 gene. On the agarose gel shown in FIG. 12D, the PCR fragments coding for the TEM-PA hybrid proteins have been loaded, where 1 to 3 repeated domains of the protein A were internalised.

The productions of the various TEM-PA hybrid proteins were achieved in the *E. coli* JM109 strain. After a 24-hours fermentation at 37° C. in a rich medium, TEM-PA hybrid proteins were overproduced in the periplasm of the bacteria. However the SDS-PAGE gel analysis shows that the hybrid proteins are partly proteolysed during their biosynthesis. The hybrid proteins were then affinity chromatography purified on IgG-sepharose (FIG. 12E) until homogeneity was reached. This showed that the domains of the protein A internalised in TEM-1 retained their affinity for the antibodies Fc region. Hydrolysis tests on the chromogenic substrate nitrocefin (red cephalosporin, antibiotic with a β-lactam ring) reveal that the hybrid proteins also retain β-lactamase activity after purification.

In order to check if the TEM-PA chimeras can be used to quantify the antibodies, ELISAs were developed in which increasing levels of rabbit IgG were immobilised on a polystyrene microplate by alkaline pH absorption ($Na_2CO_3$ 1.59 g/l, $NaHCO_3$ 2.93 g/l, pH 9.6). After saturation ($PO_4^-$ 50 mM, NaCl 150 mM, Tween-20 0.05%, Non-fat dried Milk 3%, pH7.5), a fixed amount of TEM-PA hybrid protein was added ($PO_4^-$ 50 mM, NaCl 150 mM, Tween-20 0.05%, Non-fat dried Milk 1%, pH 7.5) where one repeated domain of the protein A was internalised. After washing (3×—$PO_4^-$ 50 mM, NaCl 150 mM, Tween-20 0.05%, Non-fat dried Milk 1%, pH 7.5; 1×—$PO_4^-$ 50 mM, NaCl 150 mM, pH 7.5), red cephalosporin (100 µM) was added. In this test, the β-lactamase activity gave rise to a red colour which was followed at 482 nm. FIG. 13 shows the possibility of detecting between 10 and 100 ng of rabbit IgG after a 1 h development. The sensitivity of this test should be further increased by using a chimera protein containing several repeated domains of the protein A.

Example 11

Construction of the Hybrid Proteins of the BlaP β-Lactamase where 1 to 3 Repeated Domains of *Staphylococcus aureus* Protein A are Internalised (BlaP-PA)

The BlaP-PA chimerical partner were constructed and purified according to the same procedure described in example 10 for the TEM-1 β-lactamase. The BlaP β-lactamase is used as carrier of peptide fragment and the exogenous peptides are internalised at the site 211 (211/SmaI). The resulting hybrid β-lactamase retains its activity and also the internalised protein A is functional.

Example 12

Construction of the Hybrid Proteins of the TEM-1 β-Lactamase where the B1 and/or B2 Domain or Domains of the *Streptococcus pyogenes* Protein G are Internalised (TEM-PG)

The aim was to internalise one or more repeated domains of the protein G in position 197 of the TEM-1 β-lactamase (197/SmaI). The protein G is composed of 2 repeated domains, called B1 and B2. They confer an affinity for the antibodies Fc region (FIG. 14A). Each of the two domains is organised with a β sheet and a α helices (FIG. 14B) interacting with the CH2 and CH3 domains of the Fc region of the IgG.

The methodology used to construct TEM-PG hybrid proteins is exactly the same as the one described in example 10 for TEM-PA, apart from the following observations:

The primers used are: 5'-GGCTGTACTTACAAAT-TAATCCTTAATGGTAAAACATTG-3' (SEQ ID NO: 13) and 5'-CTCTCTTTCAGTTACCGTAAAGGTCT-TAGTCGC-3' (SEQ ID NO: 14). The structural gene used as a matrix during the PCR originates from the genomic DNA of *Streptococcus pyogenes* strain isolated at the Centre for Protein Engineering. In order to reduce the steric constraints the following amino acid residues were added on either side of the fragment. Gly Cys for the N-terminal part and Arg Glu for the C-terminal end.

At the end of the screening stages, TEM-1 β-lactamases was isolated where 1 or 2 repeated domains of the protein G were internalised (FIG. 14C). The affinity of the TEM-PG chimera proteins for the IgG immobilised on the sepharose column shows that the internalised domains of proteins G are always functional (FIG. 14E). Hydrolysis tests on the chromogenic substrate nitrocefin (antibiotic with a β-lactam nucleus) show that the TEM-PG chimeras purified on IgG-sepharose retain the β-lactamase activity. The tests showed that the internalised domains of protein G were functional.

Example 13

Construction of the Hybrid Proteins of the BlaP β-Lactamase where the B1 and/or B2 Domain or Domains of the *Streptococcus pyogenes* Protein G are Internalised (BlaP-PG)

The BlaP-PG chimera proteins were constructed and purified according to the same procedure as the one described in example 11 and 12. The BlaP β-lactamase (211/SmaI) was used as a carrier protein. The chimeras purified on IgG-sepharose retain the β-lactamase activity. The tests also showed that the internalised domains of protein G were functional.

Example 14

Construction of the Hybrid Proteins of the BlaP β-Lactamase where a Linear Epitope of the Influenza Virus Hemagglutinin is Internalised (BlaP-HA)

In order to create this hybrid protein, complementary primers (5'-AGGTTTTATCCATACGACGTCCCGGACTACGCCACAACT-3' SEQ ID NO: 15, 5'-AGTTGTGGCGTAGTCCGGGACGTCGTATGGATAAAACCT-3' SEQ ID NO: 16) were created that code for a linear epitope (HA) of the Influenza virus hemagglutinin (YPYDVPDYA). Here and there on the coding region for the epitope, two codons which code for Arg Phe and Thr Thr amino acids were added at the beginning and at the end of epitope, respectively. In this experiment, the polypeptide internalised in BlaP comprises 15 amino acids 4 of which are used for steric constraints (FIG. 15).

The two primers were hybridised and inserted into the BlaP gene (211/SmaI) which was cloned beforehand in the pROGENO-1 expression vector and digested by SmaI. After transformation, the bacteria were selected on LB agar plate+Spectinomycin (100 μg/ml final) and cephaloridin (50 μg/ml). At the end of the screening stage, BlaP β-lactamases were isolated where the epitope HA was internalised. The BlaP-HA hybrid protein was then overproduced in *E. coli* as a result of the pROGENO-1 expression vector. After extracting the periplasmic fraction by cold osmotic shock, the BlaP-HA chimera was partly purified on S-sepharose Fast Flow (SFF) in sodium acetate buffer (20 mM, pH 4.5) and eluted with a NaCl gradient. The SDS-PAGE gel featured in FIG. 16 shows the BlaP and BlaP-HA hybrid protein after SFF purification.

The antigenicity of the HA epitope internalised in BlaP was controlled by a Western Blot reaction using a specific monoclonal antibody of this hemagglutinin's epitope (rat anti-HA IgG1, 3F10, Roche). FIG. 17 shows that the monoclonal anti-HA antibody recognised the denatured BlaP-HA chimera and no cross-reaction with wild-type BlaP was detected.

The aforementioned Western Blot experiment shows that the HA epitope is recognised when the BlaP-HA chimera protein is denatured. In order to check that the anti-HA antibody also recognises the HA epitope when it is internalised in an non-denatured BlaP form an ELISA reaction was performed in which increasing quantities of rat anti-HA IgG1 were immobilised (not linked to the peroxydase, 3C10, Roche) ($Na_2CO_3$ 1.59 g/l, $NaHCO_3$ 2.93 g/l, pH 9.6). After saturation (Tris 50 mM, NaCl 0.5 M, Tween-20 0.05%, Non-fat dried Milk 1%, pH7.6), a fixed amount of BlaP-HA chimera protein was added (Tris 50 mM, NaCl 150 mM, Tween-20 0.05%, Non-fat dried Milk 1%, pH 7.6). After washing (3×—Tris 50 mM, NaCl 0.5 M, Tween-20 0.05%, Non-fat dried Milk 1%, pH 7.6; 1×—Tris 50 mM, NaCl 0.5 M, pH 7.6), red cephalosporin (100 μM) was added. FIG. 18 shows the possibility of detecting between 10 and 100 ng of rat anti-HA IgG1 after 1 h of development. This demonstrates that β-lactamase activity can be used to quantify interaction between antibody and antigen/epitope fragment.

Example 15

Construction of the Hybrid Proteins of the TEM-1 β-Lactamase where Fragments of Human Phospholipase—Type II, $hPLA_2$ are Internalised (TEM-PLA2)

In order to internalise random fragments of the human phospholipase—type II gene, $hPLA_2$ in the TEM-1 β-lactamase, the $hPLA_2$ gene was amplified by PCR. The PCR reaction was applied with the following primer: 5'-CTCGAGAAAAGAAATTTGGTGAATTTCCAC-3' (SEQ ID NO: 17) and 5'-GCAACGTGGAGTGCTCCCTCTGCAGTGTTT-3' (SEQ ID NO: 18) (95° C.-180 sec; 95° C.-30 sec, 65° C.-60 sec, 72° C.-60 sec 35 cycles, mixture of Taq polymerase/Pfu polymerase). After purification, the PCR product was digested with DNAse so as to produce DNA fragments between 50 and 430 bp. This stage may be replaced by a nebulisation reaction. The DNA fragments were then purified, blunt ended by the action of the Pfu polymerase then dephosphorylated by Calf intestine phosphatase and shotgun cloned in the TEM-1 β-lactamase carried by the expression vector pROGENO-1. At the end of the screening stages, several TEM-1 β-lactamases chimeras were isolated where fragments of varying sizes originated from the $hPLA_2$ gene were internalised (FIG. 19). In the case of three of them, sequencing reaction was applied in order to identify the $hPLA_2$ regions which were internalised (FIG. 20). In the case of the first chimera, the N-terminal domain of the $hPLA_2$ (residues 1 to 45) had been internalised. This peptide fragment contains the calcium binding site and some residues of the active site. In the second chimera, an internal fragment of the $hPLA_2$ (residues 40 to 66), covering the residues of the active site were internalised. In the third chimera, all the $hPLA_2$ protein, except for the 20 last residues, were internalised (FIG. 20). It is important to stress that the β-lactamase activity is retained for each one of the chimera selected. Trials involving the binding of calcium and measuring phospholipase activity were successful.

Example 16

Construction of a Hybrid Protein of the BlaP β-Lactamase where Fragments of Multimerised Polypeptides Comprising Three Amino Acids Repeated in Tandem and Presenting an Affinity for Bacterial Endotoxins are Internalised (BlaP-LPS)

In order to construct a new LPS-binding peptide, first of all two complementary primers corresponding to the LPS-binding amino acid sequence (Pro Ile Ile Lys Leu Leu Lys Leu Leu Lys Leu Leu Arg Arg Lys Leu Leu Lys Leu Leu Lys Leu Leu Pro Asp Gln Glu Phe Lys Gln) (SEQ ID NO: 36) were hybridised. Primer sequence: 5'-CCGATCATCAAACTTCT-CAAGCTGCTTAAACTCCTGCGCCG-GAAACTTCTCAAGCTG CTTAAACTCCTGCCGGATCAGGAGTTTAAGCAG-3' (SEQ ID NO: 19) and 5'-CTGCTTAAACTCCTGATCCG-GCAGGAGTTTAAGCAGCT-TGAGAAGTTTCCGGCGCAG GAGTTTAAGCAGCT-TGAGAAGTTTGATGATCGG-3' (SEQ ID NO: 20). Hybridisation is achieved by heat denaturation followed by a slow cooling stage. Double stranded oligonucleotide was inserted in the gene of the BlaP β-lactamase that was cloned beforehand in the expression vector pROGENO-1 and digested by SmaI. After transformation, the bacteria were selected on LB agar plate+Spectinomycin (100 µg/ml final) and cephaloridin (50 µg/ml). At the end of the screening stages, BlaP β-lactamases were isolated where LPS-binding domain was internalised. The affinity of the BlaP-LPS chimera proteins for LPS is now being characterised. Hydrolysis tests on the chromogenic substrate nitrocefin reveal that the BlaP-LPS chimeras also retain β-lactamase activity.

Example 17

Exploitation of the Hybrid Protein TEM-PA in Electrobiochemical Biosensor System The term biosensor has been applied to devices either used to monitor living systems, or to incorporate biologic or biomimetic elements. Here, in this application a "biosensor" is used in the context of a sensor incorporating a biological element such as an enzyme, antibody, nucleic acid, microorganism or cell.

The usual aim of a biosensor is to produce either discrete or continuous digital electronic signals which are proportional to a single analyte or a related group of analytes.

Experimental procedure: A polyaniline (Pani) film is electropolymerised on a platinum foil (1×0.5 cm) on the basis of a 1 M $HClO_4$ solution containing 0.1 M aniline, by potential sweeps between −0.2 and 0.8 V/SCE to 20 mV/s. The Pani film is functionalised in an electrochemical bath containing a 1 M $HClO_4$ solution, 0.05M in 3-aminophenol and 0.05 M aniline with potential sweeps between −0.2 and 0.8 V/SCE to 20 mV/s. The film is then immersed in an acetonitrile solution (4 ml) containing 0.2 ml of triethylamine, 0.04 g of disuccinimidyl carbonate and 0.01 g of dimethylaminopyridine (DMAP) for one night at ambient temperature.

The rabbit antibodies (IgG) are immobilised on the functionalised film for one night in a pH=8 phosphate buffer and 300 µl of a 4 mg/ml IgG solution. The IgG assay is achieved as follows: 50 µl of a solution of the TEM-PA hybrid protein (1 µg/µl) are deposited on the electrode (Pt/Pani/Pani-R/IgG) for 15 min, the electrode is rinsed by 3×5 ml pH=8 phosphate buffer. The potentiometric measurement is achieved in a simple compartment cell containing 4.5 ml 0.1M NaCl solution and a calomel reference electrode (SCE). The working electrode and reference are connected to a multimeter and all the potential values are collected every 30 seconds (FIG. 21). Benzylpenicillin is added every minute so that each addition produces a substrate concentration in the bath ranging from $2.6 \cdot 10^{-4}$ M to $2.6 \cdot 10^{-1}$ M.

Example 18

A Hybrid Protein of the β-Lactamase AmpC in which One Fc-Binding Domain of the *Staphylococcus aureus* Protein A is Internalised (AmpC-PA)

In this example a hybrid protein of the β-lactamase AmpC is constructed having one Fc-binding domain of the *Staphylococcus aureus* protein A internalised (AmpC-PA).

The blunt end restriction site ScaI (AGT ACT) was introduced between the Leu241 and the Asp242 position. *E. coli* production assays have shown that the new AmpC hybrid protein retains its β-lactamase activity after the restriction site (which represents the codons for Ser and Thr on the protein level) has been internalised.

The AmpC-PA hybrid partners were constructed and purified according to the procedure described in example 10 for β-lactamase TEM-1 in the present patent. The resulting hybrid β-lactamase retains its enzymatic activity and also the internalised protein A is functional as noted after affinity chromatography on IgG-sepharose. This showed that the internalised domains of the protein A retained their affinity for the Fc region of the antibodies suggesting that they are correctly folded. The AmpC-PA hybrid protein was used to quantify coated antibodies by ELISA method. Rabbit IgG were coated on a polystyrene microplate by alkaline pH absorption ($Na_2CO_3$ 1.59 g/l, $NaHCO_3$ 2.93 g/l, pH 9.6). After saturation ($PO_4^-$ 50 mM, NaCl 150 mM, Tween-20 0.05%, Non-fat dried Milk 3%, pH7.5), a fixed amount of AmpC-PA hybrid protein was added ($PO_4^-$ 50 mM, NaCl 150 mM, Tween-20 0.05%, Non-fat dried Milk 1%, pH 7.5). The hybrid protein used in this assay contained one repeated domain of the protein A. After washing (3×$PO_4^-$ 50 mM, NaCl 150 mM, Tween-20 0.05%, Non-fat dried Milk 1%, pH 7.5; 1×$PO_4^-$ 50 mM, NaCl 150 mM, pH 7.5), 150 µl of nitrocefin (100 µM) was added. In this test, the β-lactamase activity gave rise to a red colour which was followed at 482 nm. FIG. 22 shows a detection threshold between 5 to 100 ng of rabbit IgG after 30 min development.

Example 19

A Hybrid Protein of β-Lactamase BlaR-CTD Wherein a Linear Antigenic Determinant of the Hemagglutinin of the Influenza Virus is Internalised (CTD-HA)

The BlaR protein is the penicillin receptor involved in the induction of the *Bacillus licheniformis* BlaP β-lactamase. The C-terminal domain of BlaR (256 last residues) named BlaR-CTD acts as a penicillin sensor and forms with β-lactam antibiotics a very stable acyl-enzyme compound. BlaR-CTD sequence (256 residues) compared to class D Oxa-2 β-lactamase (255 residues) shows 36% identity. The superposition of the 3D structures showed that these two proteins share the same folding confirming that BlaR-CTD belongs to class D β-lactamase family. The BlaR-CTD advantage is to have a very low deacylation kinetic constant that allows fixing BlaR-CTD on a surface covered with a β-lactam.

For the construction a 45 pb fragment containing the DNA sequence coding for the HA peptide flanked by two linkers of 3 residues was introduced. In the final construct (BlaR-CTD_F514-HA), two restriction sites BamHI and KpnI are introduced between the codon coding for Phe514 and the Lys515 in the BlaR-CTD gene. The SEQ ID NO 37 shows the inserted sequence of HA peptide including the linker covering the BamHI and KpnI site, respectively.

*Bacillus subtilis* production assays have shown that the new BlaR-CTD_F514-HA hybrid protein retains its capacity to be acylated by β-lactam antibiotic and the HA peptide can be recognized by rabbit anti-HA monoclonal antibodies. The same 45 pb DNA fragment has been inserted in 3 other sites of BlaR-CTD (between E511 and F512, N532 and G533, A561 and D562). Those 3 other sites are also permissive for a HA peptide insertion. These experiments represent the first results showing permissive sites in class D β-lactamase family.

Example 20

Hybrid Proteins of β-Lactamase BlaR-CTD Wherein One Repeated Domain of the *Staphylococcus aureus* Protein A was Internalised (BlaR-CTD-PA)

A 42 pb BamHI-KpnI fragment of the BlaR-CTD_F514-HA gene was substituted by a 204 pb BamHI-KpnI fragment containing the coding sequence for one repeated domain of the protein A (PA) in order to generate BlaR-CTD_F514-PA gene. The hybrid protein has been produced by a recombinant *Bacillus subtilis* strain and exported in the extracellular medium. In crude extracellular extract, BlaR-CTD_F514-PA hybrid retains its capacity to bind fluorescent ampicillin (fluorescent β-lactam) and antibody FC-domain as shown in FIG. 23.

The BlaR-CTD_F514-PA acylated or not by fluorescent ampicillin was immobilized on a membrane by slot-blot experiment. After saturation with non-fat dried milk 3%, Donkey anti-rabbit IgG coupled to horseradish peroxydase (Amersham Bioscience) were added. After washing and addition of ECL Immunodetection reagent (Amersham Bioscience) the slot-blot was revealed after 5 minutes. In the figure, (A) represents non acylated (A) and (B) represents acylated with Fluorescent ampicillin BlaR-CTD F514-PA with fluorescent ampicillin.

REFERENCES

1: Legendre D, Vucic B, Hougardy V, Girboux A L, Henrioul C, Van Haute J, Soumillion P, Fastrez J. TEM-1 β-lactamase as a scaffold for protein recognition and assay. Protein Sci. 2002 June; 11(6):1506-18.
2: Legendre D, Soumillion P, Fastrez J. Engineering a regulatable enzyme for homogeneous immunoassays. Nat. Biotechnol. 1999 January; 17(1):67-72.
3: Vanwetswinkel S, Touillaux R, Fastrez J, Marchand-Brynaert J. Bifunctional activity labels for selection of filamentous bacteriophages displaying enzymes. Bioorg Med Chem. 1995 July; 3(7):907-15.
4: Vanwetswinkel S, Fastrez J, Marchand-Brynaert J. Synthesis of new sulfonylamido-penicillanic acid sulfones inhibitors of β-lactamases. J Antibiot (Tokyo). 1994 September; 47(9):1041-51.
5: Soumillion P, Jespers L, Bouchet M, Marchand-Brynaert J, Winter G. Fastrez J. Selection of β-lactamase on filamentous bacteriophage by catalytic activity. J Mol Biol. 1994 Apr. 8; 237(4):415-22.
6: Guillaume G, Vanhove M, Lamotte-Brasseur J, Ledent P, Jamin M, Joris B, Frere J M. Site-directed mutagenesis of glutamate 166 in two β-lactamases. Kinetic and molecular modeling studies. J Biol Chem. 1997 Feb. 28; 272(9): 5438-44.
7: Galameau A, Primeau M, Trudeau L E, Michnick S W. β-lactamase protein fragment complementation assays as in vivo and in vitro sensors of protein interactions. Nat Biotechnol. 2002 June; 20(6):619-22.
8: Hakimelahi G H, Shia K S, Pasdar M, Hakimelahi S, Khalafi-Nezhad A, Soltani M N, Mei N W, Mei H C, Saboury A A, Rezaei-Tavirani M, Moosavi-Movahedi A A. Design, synthesis, and biological evaluation of a cephalosporin-monohydroguaiaretic acid prodrug activated by a monoclonal antibody-β-lactamase conjugate. Bioorg Med Chem. 2002 September; 10(9):2927-32.
9: Melton R G, Sherwood R F. Antibody-enzyme conjugates for cancer therapy. J Natl Cancer Inst. 1996 Feb. 21; 88(34):153-65. Review.
10: Spotts, James M.; Dolmetsch, Ricardo E.; Greenberg, Michael E. Division of Neuroscience, John F. Enders. Time-lapse imaging of a dynamic phosphorylation-dependent protein-protein interaction in mammalian cells. Proceedings of the National Academy of Sciences of the United States of America (2002), 99(23), 15142-15147. CODEN: PNASA6 ISSN: 0027-8424.
11: Simon H, Voronov A V, Kvetkauskaite R, Lang H. J. A simple ELISA procedure for HIV-1 based on the enzyme β-lactamase. Immunol Methods 1991 Jun. 24; 140(1):85-92
12: Geetha P B, Ghosh S N, Gupta N P, Shaikh B H, Dandawate C N. Enzyme linked immunosorbent assay (ELISA) using β-lactamase for the detection of antibodies to KFD virus. Indian J Med Res 1980 March; 71:329-32
13: Patel S B, Khatkhatay I, Desai M P, Betrabet S S, Toddywalla V S. A sensitive ELISA for 6 β-hydroxycortisol in urine using enzyme penicillinase (β-lactamase). J Steroid Biochem Mol Biol 1994 February; 48(2-3):293
14: Hayes F, Hallet B, Cao Y. Insertion mutagenesis as a tool in the modification of protein function. Extended substrate specificity conferred by pentapeptide insertions in the omega-loop of TEM-1 β-lactamase. J Biol Chem 1997 Nov. 14; 272(46):28833-6.
15: Hallet B, Sherraft D J, Hayes F. Pentapeptide scanning mutagenesis: random insertion of a variable five amino acid cassette in a target protein. Nucleic Acids Res 1997 May 1; 25(9):1866-7;
16: Si Jae Park and San Yup Lee Efficient recovery of secretory recombinant protein from protease negative mutant *Escherichia coli* strains. Biotechnology Techniques, Vol. 12, No 11, November 1998, pp. 815-818
17: Baneyx F, Schmidt C, Georgiou G. Affinity immobilization of a genetically engineered bifunctional hybrid protein. Enzyme Microb. Technol. 1990.12, 337-42.
18: Yuqiang Wang, Huiling Yuan, Susan C Wright, Hong Wang and James W Larrick Synthesis and preliminary cytotoxicity study of a cephalosporin-CC-1065 analogue prodrug. BMC Chemical Biology 2001.

The invention claimed is:

1. A recombinant nucleotide sequence which codes upon expression a bifunctional hybrid active-site serine β-lactamase protein, wherein the β-lactamase protein is a class A, C or D β-lactamase protein that bears at least one heterologous sequence in a region located between two neighboring alpha helices of the β-lactamase sequence, wherein the region is selected from the group consisting of:
   a) a region forming a juncture between alpha helix 8 and alpha helix 9 of TEM-1 β-lactamase; and
   b) a region forming a juncture between the alpha helices of said class A, C or D β-lactamase, said alpha helices corresponding to the alpha helix 8 and alpha helix 9 of the TEM-1 β-lactamase,
   wherein the hybrid protein has two functions, wherein, in said bifunctional hybrid protein, the first function is associated with the β-lactamase portion and the second function is associated with the at least one heterologous sequence having a biological function which is different from the first function.

2. The recombinant nucleotide sequence according to claim 1, wherein the β-lactamase moiety is a class A β-lactamase, wherein said β-lactamase class A protein bears the at least one heterologous sequence in the region forming a juncture between alpha helix 8 and alpha helix 9.

3. The recombinant nucleotide sequence according to claim 1, wherein the region forming a juncture between alpha helix 8 and alpha helix 9 is selected from the group consisting of:
   a) amino acid sequence Thr195 to Leu199 of the TEM-1 β-lactamase; and
   b) an amino acid sequence in a β-lactamase other than TEM-1 β-lactamase corresponding to the amino acid sequence Thr195 to Leu199 in TEM-1 β-lactamase.

4. A recombinant nucleotide sequence which codes upon expression a bifunctional hybrid class A β-lactamase protein, wherein the class A β-lactamase protein bears at least one heterologous sequence in a region located between two neighboring alpha helices of the β-lactamase sequence, wherein the region is selected from the group consisting of:
   a) a region forming a juncture between alpha helix 8 and alpha helix 9 of the TEM-1 β-lactamase; and
   b) a region forming a juncture between the alpha helices of said class A β-lactamase, said alpha helices corresponding to the alpha helix 8 and alpha helix 9 of the TEM-1 β-lactamase,
   wherein the hybrid protein has a first function and a second function, wherein the first function is associated with the β-lactamase portion and is selected from the group consisting of:
   c) hydrolyzing β-lactams β-lactamase activity); and
   d) binding covalently and in a stable manner to substances selected from the group consisting of β-lactams, derivatives of β-lactams, and inhibitors of β-lactams;
   and wherein the second function is associated with the at least one heterologous sequence having a biological function which is different from the first function.

5. The recombinant nucleotide sequence according to claim 1, wherein the at least one heterologous sequence has a length of 11 or more amino acid residues.

6. The recombinant nucleotide sequence according to claim 1, wherein the at least one heterologous sequence has a length of 18 or more amino acid residues.

7. The recombinant nucleotide sequence according to claim 1, wherein the at least one heterologous sequence has a length of 25 or more amino acid residues.

8. The recombinant nucleotide sequence according to claim 1, wherein the at least one heterologous sequence has a length of 50 or more amino acid residues.

9. The recombinant nucleotide sequence according to claim 1, wherein the at least one heterologous sequence has a length of 100 or more amino acid residues.

10. The recombinant nucleotide sequence according to claim 1, wherein the nucleotide sequence coding for the β-lactamase comprises SEQ ID NO: 2 and encodes β-lactamase BlaP.

11. The recombinant nucleotide sequence according to claim 1, wherein the at least one heterologous sequence is selected from the group consisting of: an epitope, a specific binding partner for antibodies, a sequence that is specifically recognized and bound by antibodies, a sequence having a binding affinity to earth alkali and metal ions, a sequence having enzymatic activity, a toxin, STa heat-stable enterotoxin of *E. coli*, a glycosylation site, a glycosylated peptide, a specific binding partner for any polypeptide or any ligand, and a sequence having a binding affinity to dsDNA, ssDNA or RNA.

12. The recombinant nucleotide sequence according to claim 1, wherein at least one nucleic acid sequence encoding the at least one heterologous sequence comprises SEQ ID NO: 25 and encodes protein A of *Staphylococcus aureus* with two Fc Binding domains.

* * * * *

UNITED STATES PATENT AND TRADEMARK OFFICE
CERTIFICATE OF CORRECTION

| | |
|---|---|
| PATENT NO. | : 7,745,193 B2 |
| APPLICATION NO. | : 10/589233 |
| DATED | : June 29, 2010 |
| INVENTOR(S) | : Giannotta et al. |

It is certified that error appears in the above-identified patent and that said Letters Patent is hereby corrected as shown below:

At the Title Page, (Item 56) right column, line 11, please delete "eta 1.," and insert therefore, --et al.,--

At the Title Page, (Item 56) right column, line 16, please delete "virua-1," and insert therefore, --virus-1,--.

At the Title Page, (Item 56) right column, line 33, please delete "Curent" and insert therefore, --Current--.

At Drawing Sheet 14 of 21 (Figure 14 A B C D), please delete "14 A B C D" and insert therefore, --14 A, B, C, D--.

At column 1, line 32, please delete "1345-58.)" and insert therefore, --1345-58)--.

At column 4, line 30 (approx), please delete "47." and insert therefore, --47) respectively, in AmpC, and defined by alpha helices which correspond to those in β-lactamases of the same class or of classes A and D --

At column 6, line 56, please delete "β-lactamase" and insert therefore, --(β-lactamase--.

At column 8, line 37, please delete "SuraI)" and insert therefore, --SmaI)--.

At column 8, line 39, please delete "hPLA2" and insert therefore, --hPLA$_2$--.

At column 9, line 67, please delete "TEM-β" and insert therefore, --TEM-1 β--.

At column 13, line 27, please delete "Influenca" and insert therefore, --Influenza--.

At column 14, line 35, please delete "TEM-1 Gβ" and insert therefore, --TEM-1 β--.

At column 15, line 18, please delete "homolgous" and insert therefore, --homologous--.

At column 16, line 21 (approx), please delete "tested:" and insert therefore, --tested;--.

At column 16, line 57, please delete "potentimetric" and insert therefore, --potentiometric--.

At column 17, line 2, please delete "thyphimurium," and insert therefore, --typhimurium--.

At column 18, line 14, please delete "is" and insert therefore, --it--.

At column 19, line 15 (approx), please delete "hydrids" and insert therefore, --hybrids--.

At column 19, line 30, please delete "glutathion-5-transferase" and insert therefore, --glutathione-S-transferase--.

At column 19, line 40, please delete "Beta-lactamase" and insert therefore, --β-lactamase--.

At column 20, line 28, please delete "anti-Sta" and insert therefore, --anti-STa--.

At column 20, line 51, please delete "t a" and insert therefore, --to a--.

Signed and Sealed this
Eighteenth Day of January, 2011

David J. Kappos
*Director of the United States Patent and Trademark Office*

CERTIFICATE OF CORRECTION (continued)
U.S. Pat. No. 7,745,193 B2

At column 21, line 55, please delete "I/c" and insert therefore, --I/C--.
At column 21, line 63, please delete "197Sta" and insert therefore, --197STa--.
At column 22, line 7 (approx), please delete "I/c" and insert therefore, --I/C--.
At column 24, line 55, please delete "P" and insert therefore, --β--.
At column 26, line 10, please delete "peroxydase," and insert therefore, --peroxidase,--.
At column 29, line 41, please delete "peroxydase" and insert therefore, --peroxidase--.
At column 30, line 12 (approx), please delete "protein" and insert therefore, --protein protein--.
At column 30, line 25, please delete "88(34)" and insert therefore, --88(3-4)--.
At column 30, line 37, please delete "92" and insert therefore, --92.--.
At column 30, line 41, please delete "32" and insert therefore, --32.--.
At column 30, line 46 (approx), please delete "293" and insert therefore, --293-6.--.
At column 30, line 52, please delete "Sherraft" and insert therefore, --Sherratt--.
At column 30, line 55 (approx), please delete "7;" and insert therefore, --7.--.
At column 30, line 60, please delete "818" and insert therefore, --818.--.
At column 68, line 5 in Claim 12, please delete "β-lactamase" and insert therefore, --(β-lactamase--.

SEQUENCE LISTING

<160> NUMBER OF SEQ ID NOS: 68

<210> SEQ ID NO 1
<211> LENGTH: 858
<212> TYPE: DNA
<213> ORGANISM: Escherichia coli

<400> SEQUENCE: 1

```
ccaatgctta atcagtgagg cacctatctc agcgatctgt ctatttcgtt catccatagt      60
tgcctgactc cccgtcgtgt agataactac gatacgggag ggcttaccat ctggccccag     120
tgctgcaatg ataccgcgag acccacgctc accggctcca gatttatcag caataaacca     180
gccagccgga agggccgagc gcagaagtgg tcctgcaact ttatccgcct ccatccagtc     240
tattaattgt tgccgggaag ctagagtaag tagttcgcca gttaatagtt gcgcaacgt      300
tgttgccatt gctgcaggca tcgtggtgtc acgctcgtcg tttggtatgg cttcattcag     360
ctccggttcc caacgatcaa ggcgagttac atgatccccc atgttgtgca aaaaagcggt     420
tagctccttc ggtcctccga tcgttgtcag aagtaagttg gccgcagtgt tatcactcat     480
ggttatggca gcactgcata attctcttac tgtcatgcca tccgtaagat gcttttctgt     540
gactggtgag tactcaacca agtcattctg agaatagtgt atgcggcgac cgagttgctc     600
ttgcccggcg tcaacacggg ataataccgc gccacatagc agaactttaa aagtgctcat     660
cattggaaaa cgttcttcgg ggcgaaaact ctcaaggatc ttaccgctgt tgagatccag     720
ttcgatgtaa cccactcgtg cacccaactg atcttcagca tctttactt tcaccagcgt      780
ttctgggtga gcaaaaacag gaaggcaaaa tgccgcaaaa aagggaataa gggcgacacg     840
gaaatgttga atactcat                                                   858
```

<210> SEQ ID NO 2
<211> LENGTH: 921
<212> TYPE: DNA
<213> ORGANISM: Bacillus licheniformis

<400> SEQUENCE: 2

```
atgaaattat ggttcagtac tttaaaactg aaaaaggctg cagcagtgtt gcttttctct      60
tgcgtcgcgc ttgcaggatg cgctaacaat caaacgaatg cctcgcaacc tgccgagaag     120
aatgaaaaga cggagatgaa agatgatttt gcaaaacttg aggaacaatt tgatgcaaaa     180
ctcgggatct ttgcattgga tacaggtaca aaccggacgg tagcgtatcg gccggatgag     240
cgttttgctt ttgcttcgac gattaaggct ttaactgtag gcgtgctttt gcaacagaaa     300
tcaatagaag atctgaacca gagaataaca tatacacgtg atgatcttgt aaactacaac     360
ccgattacgg aaaagcacgt tgatacggga atgacgctca agagcttgc ggatgcttcg      420
cttcgatata gtgacaatgc ggcacagaat tcattctta aacaaattgg cggacctgaa      480
agtttgaaaa aggaactgag gaagattggt gatgaggtta caaatcccga acgattcgaa     540
ccagagttaa atgaagtgaa tccgggtgaa actcaggata ccagtacagc aagagcactt     600
gtcacaagcc ttcgagcctt tgctcttgaa gataaacttc caagtgaaaa acgcgagctt     660
ttaatcgatt ggatgaaacg aaataccact ggagacgcct taatccgtgc cggtgtgccg     720
gacggttggg aagtggctga taaaactgga gcggcatcat atggaacccg gaatgacatt     780
gccatcattt ggccgccaaa aggagatcct gtcgttcttg cagtattatc cagcagggat     840
aaaaaggacg ccaagtatga tgataaactt attgcagagg caacaaaggt ggtaatgaaa     900
```
gccttaaaca tgaacggcaa a                                          921

<210> SEQ ID NO 3
<211> LENGTH: 975
<212> TYPE: DNA
<213> ORGANISM: Streptomyces cacaoi

<400> SEQUENCE: 3
atgcgtatcc gtcccacccg tcgtcttctc ctcggcgcgg tcgcgccgct cgccctcgtt      60
ccgctggtgg cctgcggtca ggcgtcgggc tccgagagcg ccagcagcc cggcctcggc     120 ggttgcggga cgagcgcaca cggctcggcg gacgcccacg agaaggagtt ccgggcgctg     180
gagaagaagt cgacgcccca ccctggcgtc tacgccatcg acacccgcga cggccaggag     240
atcacccacc gggccgacga gcgcttcgcc tacggctcga ccttcaaggc cctccaggcg     300
ggcgcgatcc ttgcgcaagt tctccgagac gggcgcgaag tccggcgggg cgccgaggcc     360
gacggcatgg acaaggtggt ccactacggg caggacgcga tcctgcccaa ctcaccggtg     420
accgagaagc acgtcgcgga cggcatgtcc ctgcgcgagc tgtgcgacgc cgtcgtggcc     480
tacagcgaca caccgcggc caacctgctc ttcgaccagc tcggcggccg aaggggctca     540
acgcgggtcc tcaagcagct cggcgaccac accacgagca tggaccgcta cgagcaggag     600
ctgggctcgg ccgtccccgg cgaccccgg gacaccagca cgccgcgcgc gttcgccgag     660
gacctgcgcg ccttcgccgt cgaggacggc gagaaggccg ccctcgcgcc caacgaccgc     720
gagcagctga cgactggat gagcgggagc aggaccggcg acgcgctgat ccgggccggt     780
gtgccgaagg actggaaggt ggaggacaag agcggccagg tcaagtacgg cacccggaac     840
gacatcgccg tcgtccgccc gcccggccgc gcgccgatcg tcgtctcggt gatgagccac     900
ggcgacaccc aggacgccga ccgcacgac gagctggtgg ccgaggccgg cctcgtcgtc     960
gccgacggtc tgaag                                                     975

<210> SEQ ID NO 4
<211> LENGTH: 286
<212> TYPE: PRT
<213> ORGANISM: Escherichia coli

<400> SEQUENCE: 4

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Val Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

```
Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Ala Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285

<210> SEQ ID NO 5
<211> LENGTH: 307
<212> TYPE: PRT
<213> ORGANISM: Bacillus licheniformis

<400> SEQUENCE: 5

Met Lys Leu Trp Phe Ser Thr Leu Lys Leu Lys Lys Ala Ala Ala Val
1               5                   10                  15

Leu Leu Phe Ser Cys Val Ala Leu Ala Gly Cys Ala Asn Asn Gln Thr
            20                  25                  30

Asn Ala Ser Gln Pro Ala Glu Lys Asn Glu Lys Thr Glu Met Lys Asp
        35                  40                  45

Asp Phe Ala Lys Leu Glu Glu Gln Phe Asp Ala Lys Leu Gly Ile Phe
    50                  55                  60

Ala Leu Asp Thr Gly Thr Asn Arg Thr Val Ala Tyr Arg Pro Asp Glu
65                  70                  75                  80

Arg Phe Ala Phe Ala Ser Thr Ile Lys Ala Leu Thr Val Gly Val Leu
                85                  90                  95

Leu Gln Gln Lys Ser Ile Glu Asp Leu Asn Gln Arg Ile Thr Tyr Thr
            100                 105                 110

Arg Asp Asp Leu Val Asn Tyr Asn Pro Ile Thr Glu Lys His Val Asp
        115                 120                 125

Thr Gly Met Thr Leu Lys Glu Leu Ala Asp Ala Ser Leu Arg Tyr Ser
    130                 135                 140

Asp Asn Ala Ala Gln Asn Leu Ile Leu Lys Gln Ile Gly Gly Pro Glu
145                 150                 155                 160

Ser Leu Lys Lys Glu Leu Arg Lys Ile Gly Asp Glu Val Thr Asn Pro
                165                 170                 175

Glu Arg Phe Glu Pro Glu Leu Asn Glu Val Asn Pro Gly Glu Thr Gln
            180                 185                 190

Asp Thr Ser Thr Ala Arg Ala Leu Val Thr Ser Leu Arg Ala Phe Ala
        195                 200                 205

Leu Glu Asp Lys Leu Pro Ser Glu Lys Arg Glu Leu Leu Ile Asp Trp
    210                 215                 220

Met Lys Arg Asn Thr Thr Gly Asp Ala Leu Ile Arg Ala Gly Val Pro
```

```
                225                 230                 235                 240
Asp Gly Trp Glu Val Ala Asp Lys Thr Gly Ala Ala Ser Tyr Gly Thr
                245                 250                 255
Arg Asn Asp Ile Ala Ile Ile Trp Pro Pro Lys Gly Asp Pro Val Val
            260                 265                 270
Leu Ala Val Leu Ser Ser Arg Asp Lys Lys Asp Ala Lys Tyr Asp Asp
        275                 280                 285
Lys Leu Ile Ala Glu Ala Thr Lys Val Val Met Lys Ala Leu Asn Met
    290                 295                 300
Asn Gly Lys
305

<210> SEQ ID NO 6
<211> LENGTH: 325
<212> TYPE: PRT
<213> ORGANISM: Streptomyces cacaoi

<400> SEQUENCE: 6

Met Arg Ile Arg Pro Thr Arg Arg Leu Leu Leu Gly Ala Val Ala Pro
1               5                   10                  15
Leu Ala Leu Val Pro Leu Val Ala Cys Gly Gln Ala Ser Gly Ser Glu
            20                  25                  30
Ser Gly Gln Gln Pro Gly Leu Gly Gly Cys Gly Thr Ser Ala His Gly
        35                  40                  45
Ser Ala Asp Ala His Glu Lys Glu Phe Arg Ala Leu Glu Lys Lys Phe
    50                  55                  60
Asp Ala His Pro Gly Val Tyr Ala Ile Asp Thr Arg Asp Gly Gln Glu
65                  70                  75                  80
Ile Thr His Arg Ala Asp Glu Arg Phe Ala Tyr Gly Ser Thr Phe Lys
                85                  90                  95
Ala Leu Gln Ala Gly Ala Ile Leu Ala Gln Val Leu Arg Asp Gly Arg
            100                 105                 110
Glu Val Arg Arg Gly Ala Glu Ala Asp Gly Met Asp Lys Val Val His
        115                 120                 125
Tyr Gly Gln Asp Ala Ile Leu Pro Asn Ser Pro Val Thr Glu Lys His
    130                 135                 140
Val Ala Asp Gly Met Ser Leu Arg Glu Leu Cys Asp Ala Val Val Ala
145                 150                 155                 160
Tyr Ser Asp Asn Thr Ala Ala Asn Leu Leu Phe Asp Gln Leu Gly Gly
                165                 170                 175
Arg Arg Gly Ser Thr Arg Val Leu Lys Gln Leu Gly Asp His Thr Thr
            180                 185                 190
Ser Met Asp Arg Tyr Glu Gln Glu Leu Gly Ser Ala Val Pro Gly Asp
        195                 200                 205
Pro Arg Asp Thr Ser Thr Pro Arg Ala Phe Ala Glu Asp Leu Arg Ala
    210                 215                 220
Phe Ala Val Glu Asp Gly Glu Lys Ala Ala Leu Ala Pro Asn Asp Arg
225                 230                 235                 240
Glu Gln Leu Asn Asp Trp Met Ser Gly Ser Arg Thr Gly Asp Ala Leu
                245                 250                 255
Ile Arg Ala Gly Val Pro Lys Asp Trp Lys Val Glu Asp Lys Ser Gly
            260                 265                 270
Gln Val Lys Tyr Gly Thr Arg Asn Asp Ile Ala Val Val Arg Pro Pro
        275                 280                 285
```

```
Gly Arg Ala Pro Ile Val Val Ser Val Met Ser His Gly Asp Thr Gln
    290                 295                 300

Asp Ala Glu Pro His Asp Glu Leu Val Ala Glu Ala Gly Leu Val Val
305                 310                 315                 320

Ala Asp Gly Leu Lys
                325

<210> SEQ ID NO 7
<211> LENGTH: 36
<212> TYPE: DNA
<213> ORGANISM: Artificial Sequence
<220> FEATURE:
<223> OTHER INFORMATION: synthetic primer

<400> SEQUENCE: 7
tcagttaaca atttcaacaa agaacaacaa aatgct                           36

<210> SEQ ID NO 8
<211> LENGTH: 30
<212> TYPE: DNA
<213> ORGANISM: Artificial Sequence
<220> FEATURE:
<223> OTHER INFORMATION: synthetic primer

<400> SEQUENCE: 8
tcgaaatttt ttgttgtctt cctcttttgg                                  30

<210> SEQ ID NO 9
<211> LENGTH: 33
<212> TYPE: DNA
<213> ORGANISM: Artificial Sequence
<220> FEATURE:
<223> OTHER INFORMATION: synthetic primer

<400> SEQUENCE: 9
catatgaaaa agaaaaacat ttattcaatt cgt                              33

<210> SEQ ID NO 10
<211> LENGTH: 33
<212> TYPE: DNA
<213> ORGANISM: Artificial Sequence
<220> FEATURE:
<223> OTHER INFORMATION: synthetic primer

<400> SEQUENCE: 10
ggatccttat agttcgcgac gacgtccagc taa                              33

<210> SEQ ID NO 11
<211> LENGTH: 32
<212> TYPE: DNA
<213> ORGANISM: Artificial Sequence
<220> FEATURE:
<223> OTHER INFORMATION: synthetic primer

<400> SEQUENCE: 11
cgggagctca ggctcaccca gaaacgctgg tg                               32

<210> SEQ ID NO 12
<211> LENGTH: 36
<212> TYPE: DNA
<213> ORGANISM: Artificial Sequence
<220> FEATURE:
<223> OTHER INFORMATION: synthetic primer

<400> SEQUENCE: 12
```

-continued cgggaattct caccaatgct taatcagtga ggcacc          36

<210> SEQ ID NO 13
<211> LENGTH: 39
<212> TYPE: DNA
<213> ORGANISM: Artificial Sequence
<220> FEATURE:
<223> OTHER INFORMATION: synthetic primer

<400> SEQUENCE: 13
ggctgtactt acaaattaat ccttaatggt aaaacattg          39

<210> SEQ ID NO 14
<211> LENGTH: 33
<212> TYPE: DNA
<213> ORGANISM: Artificial Sequence
<220> FEATURE:
<223> OTHER INFORMATION: synthetic primer

<400> SEQUENCE: 14
ctctctttca gttaccgtaa aggtcttagt cgc          33

<210> SEQ ID NO 15
<211> LENGTH: 39
<212> TYPE: DNA
<213> ORGANISM: Artificial Sequence
<220> FEATURE:
<223> OTHER INFORMATION: synthetic primer

<400> SEQUENCE: 15
aggttttatc catacgacgt cccggactac gccacaact          39

<210> SEQ ID NO 16
<211> LENGTH: 39
<212> TYPE: DNA
<213> ORGANISM: Artificial Sequence
<220> FEATURE:
<223> OTHER INFORMATION: synthetic primer

<400> SEQUENCE: 16
agttgtggcg tagtccggga cgtcgtatgg ataaaacct          39

<210> SEQ ID NO 17
<211> LENGTH: 30
<212> TYPE: DNA
<213> ORGANISM: Artificial Sequence
<220> FEATURE:
<223> OTHER INFORMATION: synthetic primer

<400> SEQUENCE: 17
ctcgagaaaa gaaatttggt gaatttccac          30

<210> SEQ ID NO 18
<211> LENGTH: 30
<212> TYPE: DNA
<213> ORGANISM: Artificial Sequence
<220> FEATURE:
<223> OTHER INFORMATION: synthetic primer

<400> SEQUENCE: 18
gcaacgtgga gtgctccctc tgcagtgttt          30

<210> SEQ ID NO 19
<211> LENGTH: 90
<212> TYPE: DNA
<213> ORGANISM: Artificial Sequence

```
<220> FEATURE:
<223> OTHER INFORMATION: synthetic primer

<400> SEQUENCE: 19
ccgatcatca aacttctcaa gctgcttaaa ctcctgcgcc ggaaacttct caagctgctt      60
aaactcctgc cggatcagga gtttaagcag                                       90

<210> SEQ ID NO 20
<211> LENGTH: 90
<212> TYPE: DNA
<213> ORGANISM: Artificial Sequence
<220> FEATURE:
<223> OTHER INFORMATION: synthetic primer

<400> SEQUENCE: 20
ctgcttaaac tcctgatccg gcaggagttt aagcagcttg agaagtttcc ggcgcaggag      60
tttaagcagc ttgagaagtt tgatgatcgg                                       90

<210> SEQ ID NO 21
<211> LENGTH: 54
<212> TYPE: DNA
<213> ORGANISM: Escherichia coli

<400> SEQUENCE: 21
aacacgtttt actgctgcga actttgctgc aacccagcat gcgcaggttg ctac            54

<210> SEQ ID NO 22
<211> LENGTH: 18
<212> TYPE: PRT
<213> ORGANISM: Escherichia coli

<400> SEQUENCE: 22

Asn Thr Phe Tyr Cys Cys Glu Leu Cys Cys Asn Pro Ala Cys Ala Gly
1               5                   10                  15

Cys Tyr

<210> SEQ ID NO 23
<211> LENGTH: 201
<212> TYPE: DNA
<213> ORGANISM: Staphylococcus aureus

<400> SEQUENCE: 23
tcagtgaaca atttcaacaa agaacaacaa aatgctttct atgaaatttt acatttacct      60
aacttaactg aagaacaacg taacggcttc atccaaagcc ttaaagacga tccttcagtg     120
agcaaagaaa ttttagcaga agctaaaaag ctaaacgatg ctcaagcacc aaaagaggaa     180
gacaacaaga aaaaatttcg a                                               201

<210> SEQ ID NO 24
<211> LENGTH: 67
<212> TYPE: PRT
<213> ORGANISM: Staphylococcus aureus

<400> SEQUENCE: 24

Ser Val Asn Asn Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45
```

Lys Lys Leu Asn Asp Ala Gln Ala Pro Lys Glu Glu Asp Asn Lys Lys
 50                  55                  60

Lys Phe Arg
 65

<210> SEQ ID NO 25
<211> LENGTH: 375
<212> TYPE: DNA
<213> ORGANISM: Staphylococcus aureus

<400> SEQUENCE: 25
tcagtgaaca atttcaacaa agaacaacaa aatgctttct atgaaatctt gaacatgcct      60
aacttgaacg aagaacaacg caatggtttc atccaaagct aaaagatga cccaagtcaa     120 agtgctaacc ttttagcaga agctaaaaag ttaaatgaat ctcaagcacc gaaagctgat     180
aacaatttca caaagaaca acaaaatgct ttctatgaaa ttttacattt acctaactta     240
actgaagaac aacgtaacgg cttcatccaa agccttaaag acgatccttc agtgagcaaa     300
gaaattttag cagaagctaa aaagctaaac gatgctcaag caccaaaaga ggaagacaac     360
aagaaaaaat ttcga                                                     375

<210> SEQ ID NO 26
<211> LENGTH: 125
<212> TYPE: PRT
<213> ORGANISM: Staphylococcus aureus

<400> SEQUENCE: 26

Ser Val Asn Asn Phe Asn Lys Glu Gln Gln Asn Ala Phe Tyr Glu Ile
 1               5                  10                  15

Leu Asn Met Pro Asn Leu Asn Glu Glu Gln Arg Asn Gly Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Glu Ser Gln Ala Pro Lys Ala Asp Asn Asn Phe Asn
 50                  55                  60

Lys Glu Gln Gln Asn Ala Phe Tyr Glu Ile Leu His Leu Pro Asn Leu
 65                  70                  75                  80

Thr Glu Glu Gln Arg Asn Gly Phe Ile Gln Ser Leu Lys Asp Asp Pro
                85                  90                  95

Ser Val Ser Lys Glu Ile Leu Ala Glu Ala Lys Lys Leu Asn Asp Ala
            100                 105                 110

Gln Ala Pro Lys Glu Glu Asp Asn Lys Lys Phe Arg
        115                 120                 125

<210> SEQ ID NO 27
<211> LENGTH: 177
<212> TYPE: DNA
<213> ORGANISM: Streptococcus pyogenes

<400> SEQUENCE: 27
ggctgtactt acaaattaat ccttaatggt aaaacattga aaggccaaac aactactgaa      60
gctgttgatg ctgctactgc agaaaaagtc ttcaaacaat acgctaacga caacggtgtt     120
gacggtgaat ggacttacga cgatgcgact aagacctta cggtaactga aagagaa         177

<210> SEQ ID NO 28
<211> LENGTH: 59
<212> TYPE: PRT
<213> ORGANISM: Streptococcus pyogenes

<400> SEQUENCE: 28

| Gly | Cys | Thr | Tyr | Lys | Leu | Ile | Leu | Asn | Gly | Lys | Thr | Leu | Lys | Gly | Gln |
| 1 | | | | 5 | | | | | 10 | | | | | 15 | |

| Thr | Thr | Thr | Glu | Ala | Val | Asp | Ala | Ala | Thr | Ala | Glu | Lys | Val | Phe | Lys |
| | | | 20 | | | | | 25 | | | | | 30 | | |

| Gln | Tyr | Ala | Asn | Asp | Asn | Gly | Val | Asp | Gly | Glu | Trp | Thr | Tyr | Asp | Asp |
| | | 35 | | | | | 40 | | | | | 45 | | | |

| Ala | Thr | Lys | Thr | Phe | Thr | Val | Thr | Glu | Arg | Glu |
| | 50 | | | | 55 | | | | | |

<210> SEQ ID NO 29
<211> LENGTH: 387
<212> TYPE: DNA
<213> ORGANISM: Streptococcus pyogenes

<400> SEQUENCE: 29

```
ggctgtactt acaaattaat ccttaatggt aaaacattga aaggccaaac aactactgaa      60
gctgttgatg ctgctactgc agaaaaagtc ttcaaacaat acgctaacga caacggtgtt     120
gacggtgaat ggacttacga cgatgcgact aagacctta cagttactga aaaaccagaa     180
gtgatcgatg cgtctgaatt aaccaccagcc gtgacaactt acaaacttgt tattaatggt     240
aaaacattga aaggcgaaac aactactaaa gcagtagacg cagaaactgc agaaaaagcc     300
ttcaaacaat acgctaacga caacggtgtt gatggtgttt ggacttatga tgatgcgact     360
aagaccttta cggtaactga aagagag                                         387
```

<210> SEQ ID NO 30
<211> LENGTH: 129
<212> TYPE: PRT
<213> ORGANISM: Streptococcus pyogenes

<400> SEQUENCE: 30

| Gly | Cys | Thr | Tyr | Lys | Leu | Ile | Leu | Asn | Gly | Lys | Thr | Leu | Lys | Gly | Gln |
| 1 | | | | 5 | | | | | 10 | | | | | 15 | |

| Thr | Thr | Thr | Glu | Ala | Val | Asp | Ala | Ala | Thr | Ala | Glu | Lys | Val | Phe | Lys |
| | | | 20 | | | | | 25 | | | | | 30 | | |

| Gln | Tyr | Ala | Asn | Asp | Asn | Gly | Val | Asp | Gly | Glu | Trp | Thr | Tyr | Asp | Asp |
| | | 35 | | | | | 40 | | | | | 45 | | | |

| Ala | Thr | Lys | Thr | Phe | Thr | Val | Thr | Glu | Lys | Pro | Glu | Val | Ile | Asp | Ala |
| | 50 | | | | 55 | | | | | 60 | | | | | |

| Ser | Glu | Leu | Thr | Pro | Ala | Val | Thr | Thr | Tyr | Lys | Leu | Val | Ile | Asn | Gly |
| 65 | | | | | 70 | | | | | 75 | | | | | 80 |

| Lys | Thr | Leu | Lys | Gly | Glu | Thr | Thr | Thr | Lys | Ala | Val | Asp | Ala | Glu | Thr |
| | | | | 85 | | | | | 90 | | | | | 95 | |

| Ala | Glu | Lys | Ala | Phe | Lys | Gln | Tyr | Ala | Asn | Asp | Asn | Gly | Val | Asp | Gly |
| | | | 100 | | | | | 105 | | | | | 110 | | |

| Val | Trp | Thr | Tyr | Asp | Asp | Ala | Thr | Lys | Thr | Phe | Thr | Val | Thr | Glu | Arg |
| | | | 115 | | | | | 120 | | | | | 125 | | |

Glu

<210> SEQ ID NO 31
<211> LENGTH: 39
<212> TYPE: DNA
<213> ORGANISM: Influenza virus

<400> SEQUENCE: 31

```
aggtttatc catacgacgt cccggactac gccacaact                              39
```

<210> SEQ ID NO 32
<211> LENGTH: 13
<212> TYPE: PRT
<213> ORGANISM: Influenza virus

<400> SEQUENCE: 32

```
Arg Phe Tyr Pro Tyr Asp Val Pro Asp Tyr Ala Thr Thr
 1               5                  10
```

<210> SEQ ID NO 33
<211> LENGTH: 384
<212> TYPE: DNA
<213> ORGANISM: Homo sapiens

<400> SEQUENCE: 33

```
ctcgagaaaa gaatttggt gaatttccac agaatgatca agttgacgac aggaaaggaa       60
gccgcactca gttatggctt ctacggctgc cactgtggcg tgggtggcag aggatccccc     120
aaggatgcaa cggatcgctg ctgtgtcact catgactgtt gctacaaacg tctggagaaa     180
cgtggatgtg gcaccaaatt tctgagctac aagtttagca actcggggag cagaatcacc     240
tgtgcaaaac aggactcctg cagaagtcaa ctgtgtgagt gtgataaggc tgctgccacc     300
tgttttgcta gaaacaagac gacctacaat aaaaagtacc agtactattc aataaaacac     360
tgcagaggga gcactccacg ttgc                                            384
```

<210> SEQ ID NO 34
<211> LENGTH: 128
<212> TYPE: PRT
<213> ORGANISM: Homo sapiens

<400> SEQUENCE: 34

```
Leu Glu Lys Arg Asn Leu Val Asn Phe His Arg Met Ile Lys Leu Thr
 1               5                  10                  15

Thr Gly Lys Glu Ala Ala Leu Ser Tyr Gly Phe Tyr Gly Cys His Cys
             20                  25                  30

Gly Val Gly Gly Arg Gly Ser Pro Lys Asp Ala Thr Asp Arg Cys Cys
         35                  40                  45

Val Thr His Asp Cys Cys Tyr Lys Arg Leu Glu Lys Arg Gly Cys Gly
     50                  55                  60

Thr Lys Phe Leu Ser Tyr Lys Phe Ser Asn Ser Gly Ser Arg Ile Thr
 65                  70                  75                  80

Cys Ala Lys Gln Asp Ser Cys Arg Ser Gln Leu Cys Glu Cys Asp Lys
                 85                  90                  95

Ala Ala Ala Thr Cys Phe Ala Arg Asn Lys Thr Thr Tyr Asn Lys Lys
            100                 105                 110

Tyr Gln Tyr Tyr Ser Asn Lys His Cys Arg Gly Ser Thr Pro Arg Cys
        115                 120                 125
```

<210> SEQ ID NO 35
<211> LENGTH: 90
<212> TYPE: DNA
<213> ORGANISM: Artificial Sequence
<220> FEATURE:
<223> OTHER INFORMATION: synthetic affinity to LPS

<400> SEQUENCE: 35

```
ccgatcatca aacttctcaa gctgcttaaa ctcctgcgcc ggaaacttct caagctgctt       60
```

```
aaactcctgc cggatcagga gtttaagcag                                    90
```

<210> SEQ ID NO 36
<211> LENGTH: 30
<212> TYPE: PRT
<213> ORGANISM: Artificial Sequence
<220> FEATURE:
<223> OTHER INFORMATION: HA peptide containing linker

<400> SEQUENCE: 36

```
Pro Ile Ile Lys Leu Leu Lys Leu Leu Lys Leu Leu Arg Arg Lys Leu
1               5                   10                  15
Leu Lys Leu Leu Lys Leu Leu Pro Asp Gln Glu Phe Lys Gln
            20                  25                  30
```

<210> SEQ ID NO 37
<211> LENGTH: 15
<212> TYPE: PRT
<213> ORGANISM: Artificial Sequence
<220> FEATURE:
<223> OTHER INFORMATION: synthetic peptide

<400> SEQUENCE: 37

```
Gly Ser Gly Tyr Pro Tyr Asp Val Pro Asp Tyr Ala Gly Thr Gly
1               5                   10                  15
```

<210> SEQ ID NO 38
<211> LENGTH: 377
<212> TYPE: PRT
<213> ORGANISM: Escherichia coli

<400> SEQUENCE: 38

```
Met Phe Lys Thr Thr Leu Cys Ala Leu Leu Ile Thr Ala Ser Cys Ser
1               5                   10                  15
Thr Phe Ala Ala Pro Gln Gln Ile Asn Asp Ile Val His Arg Thr Ile
            20                  25                  30
Thr Pro Leu Ile Glu Gln Gln Lys Ile Pro Gly Met Ala Val Ala Val
        35                  40                  45
Ile Tyr Gln Gly Lys Pro Tyr Tyr Phe Thr Trp Gly Tyr Ala Asp Ile
    50                  55                  60
Ala Lys Lys Gln Pro Val Thr Gln Gln Thr Leu Phe Glu Leu Gly Ser
65                  70                  75                  80
Val Ser Lys Thr Phe Thr Gly Val Leu Gly Gly Asp Ala Ile Ala Arg
                85                  90                  95
Gly Glu Ile Lys Leu Ser Asp Pro Thr Thr Lys Tyr Trp Pro Glu Leu
            100                 105                 110
Thr Ala Lys Gln Trp Asn Gly Ile Thr Leu Leu His Leu Ala Thr Tyr
        115                 120                 125
Thr Ala Gly Gly Leu Pro Leu Gln Val Pro Asp Glu Val Lys Ser Ser
    130                 135                 140
Ser Asp Leu Leu Arg Phe Tyr Gln Asn Trp Gln Pro Ala Trp Ala Pro
145                 150                 155                 160
Gly Thr Gln Arg Leu Tyr Ala Asn Ser Ser Ile Gly Leu Phe Gly Ala
                165                 170                 175
Leu Ala Val Lys Pro Ser Gly Leu Ser Phe Glu Gln Ala Met Gln Thr
            180                 185                 190
Arg Val Phe Gln Pro Leu Lys Leu Asn His Thr Trp Ile Asn Val Pro
        195                 200                 205
Pro Ala Glu Glu Lys Asn Tyr Ala Trp Gly Tyr Arg Glu Gly Lys Ala
```

```
                210                 215                 220
Val His Val Ser Pro Gly Ala Leu Asp Ala Glu Ala Tyr Gly Val Lys
225                 230                 235                 240

Ser Thr Ile Glu Asp Met Ala Arg Trp Val Gln Ser Asn Leu Lys Pro
                245                 250                 255

Leu Asp Ile Asn Glu Lys Thr Leu Gln Gln Gly Ile Gln Leu Ala Gln
            260                 265                 270

Ser Arg Tyr Trp Gln Thr Gly Asp Met Tyr Gln Gly Leu Gly Trp Glu
        275                 280                 285

Met Leu Asp Trp Pro Val Asn Pro Asp Ser Ile Ile Asn Gly Ser Asp
290                 295                 300

Asn Lys Ile Ala Leu Ala Ala Arg Pro Val Lys Ala Ile Thr Pro Pro
305                 310                 315                 320

Thr Pro Ala Val Arg Ala Ser Trp Val His Lys Thr Gly Ala Thr Gly
                325                 330                 335

Gly Phe Gly Ser Tyr Val Ala Phe Ile Pro Glu Lys Glu Leu Gly Ile
            340                 345                 350

Val Met Leu Ala Asn Lys Asn Tyr Pro Asn Pro Ala Arg Val Asp Ala
        355                 360                 365

Ala Trp Gln Ile Leu Asn Ala Leu Gln
    370                 375

<210> SEQ ID NO 39
<211> LENGTH: 1140
<212> TYPE: DNA
<213> ORGANISM: Escherichia coli

<400> SEQUENCE: 39
atgttcaaaa cgacgctctg cgccttatta attaccgcct cttgctccac atttgctgcc      60
cctcaacaaa tcaacgatat tgtgcatcgc acaattaccc cgcttataga gcaacaaaag     120
atcccgggta tggcggtggc ggtaatttat cagggtaaac cttattactt tacctggggc     180
tatgcggaca tcgccaaaaa gcagcccgtc acacagcaaa cgttgtttga gttaggttcg     240
gtcagcaaaa catttactgg cgtgcttggt ggcgacgcta ttgctcgagg ggaaatcaag     300
ttaagcgatc ccacaacaaa atactggcct gaacttaccg ctaaacagtg gaatgggatc     360
acactattac atctcgcaac ctacactgct ggcggcctgc cattgcaggt gccggatgag     420
gtgaaatcct caagcgactt gctgcgcttc tatcaaaact ggcagcctgc atgggctcca     480
ggaacacaac gtctgtatgc caactccagt atcggtttgt tcggcgcact ggctgtgaag     540
ccgtctggtt tgagttttga gcaggcgatg caaactcgtg tcttccagcc actcaaactc     600
aaccatacgt ggattaatgt accgcccgca gaagaaaaga attacgcctg ggatatcgc     660 gaaggtaagg cagtgcatgt ttcgcctggg gcgttagatg ctgaagctta tggtgtgaag     720
tcgaccattg aagatatggc ccgctgggtg caaagcaatt taaaacccct tagtactgat     780
atcaatgaga aaacgcttca acaagggata caactggcac aatctcgcta ctggcaaacc     840
ggcgatatgt atcagggcct gggctgggaa atgctggact ggccggtaaa tcctgacagc     900
atcattaacg gcagtgacaa taaaattgca ctggcagcac gccccgtaaa agcgattacg     960 ccccaactc ctgcagtacg cgcatcatgg gtacataaaa caggggcgac cggcggattt    1020
ggtagctatg tcgcgtttat tccagaaaaa gagctgggta tcgtgatgct ggcaaacaaa    1080
aactatccca tccagcgag agtcgacgcc gcctggcaga ttcttaacgc tctacagtaa    1140
```

<210> SEQ ID NO 40
<211> LENGTH: 256
<212> TYPE: PRT
<213> ORGANISM: Bacillus licheniformis

<400> SEQUENCE: 40

Met Gln Lys Glu Thr Arg Phe Leu Pro Gly Thr Asn Val Glu Tyr Glu
1               5                   10                  15

Asp Tyr Ser Thr Phe Phe Asp Lys Phe Ser Ala Ser Gly Gly Phe Val
            20                  25                  30

Leu Phe Asn Ser Asn Arg Lys Lys Tyr Thr Ile Tyr Asn Arg Lys Glu
        35                  40                  45

Ser Thr Ser Arg Phe Ala Pro Ala Ser Thr Tyr Lys Val Phe Ser Ala
    50                  55                  60

Leu Leu Ala Leu Glu Ser Gly Ile Ile Thr Lys Asn Asp Ser His Met
65                  70                  75                  80

Thr Trp Asp Gly Thr Gln Tyr Pro Tyr Lys Glu Trp Asn Gln Asp Gln
                85                  90                  95

Asp Leu Phe Ser Ala Met Ser Ser Thr Thr Trp Tyr Phe Gln Lys
            100                 105                 110

Leu Asp Arg Gln Ile Gly Glu Asp His Leu Arg His Tyr Leu Lys Ser
        115                 120                 125

Ile His Tyr Gly Asn Glu Asp Phe Ser Val Pro Ala Asp Tyr Trp Leu
    130                 135                 140

Asp Gly Ser Leu Gln Ile Ser Pro Leu Glu Gln Val Asn Ile Leu Lys
145                 150                 155                 160

Lys Phe Tyr Asp Asn Glu Phe Asp Phe Lys Gln Ser Asn Ile Glu Thr
                165                 170                 175

Val Lys Asp Ser Ile Arg Leu Glu Glu Ser Asn Gly Arg Val Leu Ser
            180                 185                 190

Gly Lys Thr Gly Thr Ser Val Ile Asn Gly Glu Leu His Ala Gly Trp
        195                 200                 205

Phe Ile Gly Tyr Val Glu Thr Ala Asp Asn Thr Phe Phe Phe Ala Val
    210                 215                 220

His Ile Gln Gly Glu Lys Arg Ala Ala Gly Ser Ser Ala Ala Glu Ile
225                 230                 235                 240

Ala Leu Ser Ile Leu Asp Lys Lys Gly Ile Tyr Pro Ser Val Ser Arg
                245                 250                 255

<210> SEQ ID NO 41
<211> LENGTH: 768
<212> TYPE: DNA
<213> ORGANISM: Bacillus licheniformis

<400> SEQUENCE: 41
atgcaaaaag aaacacgctt tttacccggc accaatgtag aatacgaaga ttacagcact      60
ttttttgata aattttcagc ctcagggggc tttgtcctgt taattctaa taggaaaaag     120 tatacaatat acaataggaa agaaagcacc tccagattcg cacctgcttc cacctacaag     180
gtgtttagcg cattgctcgc actggaatcc gggatcatca cgaagaacga ctctcacatg     240
acttgggatg ggactcaata tccgtataaa gaatggaatc aagaccagga tttattctct     300
gcgatgagca gctccacaac atggtatttt caaaaattgg accggcaaat tggggaggat     360
catttacgtc attatctcaa atctatacat tatggaaatg aggattttc agtcccggcc     420 gattattggc tggatggctc tcttcaaatt tctccacttg aacaggtcaa tatattaaaa     480

```
aagtttatg ataacgaatt tgattttaaa cagtctaata ttgaaactgt gaaagattcg    540
atacgtttag aagaatcaaa tggcagggtt ttatccggta aaaccggaac ctcggtaatc    600
aacggggaac tccatgccgg ttggtttatc gggtatgtag aaactgccga taatactttt    660
ttctttgctg ttcatattca aggtgaaaaa cgggctgccg aagctccgc tgccgaaatt    720 gcactttcca ttttagataa aaagggatt tatccctccg tttcccga                 768
```

```
<210> SEQ ID NO 42
<211> LENGTH: 12
<212> TYPE: PRT
<213> ORGANISM: Artificial Sequence
<220> FEATURE:
<223> OTHER INFORMATION: BlaP alpha helix 8

<400> SEQUENCE: 42

Ala Arg Ala Leu Ala Thr Ser Leu Gln Ala Phe Ala
1               5                   10

<210> SEQ ID NO 43
<211> LENGTH: 12
<212> TYPE: PRT
<213> ORGANISM: Artificial Sequence
<220> FEATURE:
<223> OTHER INFORMATION: BlaP alpha helix 9

<400> SEQUENCE: 43

Ser Glu Lys Arg Glu Leu Leu Ile Asp Trp Met Lys
1               5                   10

<210> SEQ ID NO 44
<211> LENGTH: 12
<212> TYPE: PRT
<213> ORGANISM: Artificial Sequence
<220> FEATURE:
<223> OTHER INFORMATION: TEM-1 beta-lactamase alpha helix 8

<400> SEQUENCE: 44

Pro Ala Ala Met Ala Thr Thr Leu Arg Lys Leu Leu
1               5                   10

<210> SEQ ID NO 45
<211> LENGTH: 12
<212> TYPE: PRT
<213> ORGANISM: Artificial Sequence
<220> FEATURE:
<223> OTHER INFORMATION: TEM-1 beta-lactamase alpha helix 9

<400> SEQUENCE: 45

Leu Ala Ser Arg Gln Gln Leu Ile Asp Trp Met Glu
1               5                   10

<210> SEQ ID NO 46
<211> LENGTH: 12
<212> TYPE: PRT
<213> ORGANISM: Artificial Sequence
<220> FEATURE:
<223> OTHER INFORMATION: AmpC alpha helix 8

<400> SEQUENCE: 46

Ile Glu Asp Met Ala Arg Trp Val Gln Ser Asn Leu
1               5                   10

<210> SEQ ID NO 47
<211> LENGTH: 10
<212> TYPE: PRT
```

<213> ORGANISM: Artificial Sequence
<220> FEATURE:
<223> OTHER INFORMATION: AmpC alpha helix 9

<400> SEQUENCE: 47

Lys Thr Leu Gln Gln Gly Ile Gln Leu Ala
1               5                   10

<210> SEQ ID NO 48
<211> LENGTH: 10
<212> TYPE: PRT
<213> ORGANISM: Artificial Sequence
<220> FEATURE:
<223> OTHER INFORMATION: restriction cassette

<400> SEQUENCE: 48

Leu Leu Thr Gly Glu Leu Leu Thr Leu Ala
1               5                   10

<210> SEQ ID NO 49
<211> LENGTH: 30
<212> TYPE: DNA
<213> ORGANISM: Artificial Sequence
<220> FEATURE:
<223> OTHER INFORMATION: restriction cassette

<400> SEQUENCE: 49
ctattaactg gcgaactact tactctagct                                      30

<210> SEQ ID NO 50
<211> LENGTH: 12
<212> TYPE: PRT
<213> ORGANISM: Artificial Sequence
<220> FEATURE:
<223> OTHER INFORMATION: restriction cassette

<400> SEQUENCE: 50

Leu Leu Thr Gly Val Pro Leu Thr Gly Thr Leu Ala
1               5                   10

<210> SEQ ID NO 51
<211> LENGTH: 36
<212> TYPE: DNA
<213> ORGANISM: Artificial Sequence
<220> FEATURE:
<223> OTHER INFORMATION: restriction cassette

<400> SEQUENCE: 51
ctattaactg gggtacccct aactggcact ctagct                               36

<210> SEQ ID NO 52
<211> LENGTH: 24
<212> TYPE: PRT
<213> ORGANISM: Artificial Sequence
<220> FEATURE:
<223> OTHER INFORMATION: restriction cassette

<400> SEQUENCE: 52

Leu Leu Thr Gly Val Pro Pro Gly Leu Gln Leu Glu Leu Lys Pro Gly
1               5                   10                  15

Arg Tyr Pro Leu Thr Gly Glu Leu
                20

<210> SEQ ID NO 53
<211> LENGTH: 72
<212> TYPE: DNA

```
<213> ORGANISM: Artificial Sequence
<220> FEATURE:
<223> OTHER INFORMATION: restriction cassette

<400> SEQUENCE: 53
ctattaactg gggtaccgcc cgggctgcag ctcgagctta agcccgggcg gtaccccta      60 actggcgaac ta                                                        72

<210> SEQ ID NO 54
<211> LENGTH: 16
<212> TYPE: PRT
<213> ORGANISM: Artificial Sequence
<220> FEATURE:
<223> OTHER INFORMATION: restriction cassette

<400> SEQUENCE: 54

Leu Leu Thr Gly Val Pro Pro Gly Arg Tyr Pro Leu Thr Gly Glu Leu
1               5                   10                  15

<210> SEQ ID NO 55
<211> LENGTH: 48
<212> TYPE: DNA
<213> ORGANISM: Artificial Sequence
<220> FEATURE:
<223> OTHER INFORMATION: restriction cassette

<400> SEQUENCE: 55
ctattaactg gggtaccgcc cgggcggtac cccctaactg gcgaacta                  48

<210> SEQ ID NO 56
<211> LENGTH: 10
<212> TYPE: PRT
<213> ORGANISM: Artificial Sequence
<220> FEATURE:
<223> OTHER INFORMATION: restriction cassette

<400> SEQUENCE: 56

Ala Leu Glu Asp Lys Leu Pro Ser Glu Lys
1               5                   10

<210> SEQ ID NO 57
<211> LENGTH: 30
<212> TYPE: DNA
<213> ORGANISM: Artificial Sequence
<220> FEATURE:
<223> OTHER INFORMATION: restriction cassette

<400> SEQUENCE: 57
gctcttgaag ataaacttcc aagtgaaaaa                                      30

<210> SEQ ID NO 58
<211> LENGTH: 12
<212> TYPE: PRT
<213> ORGANISM: Artificial Sequence
<220> FEATURE:
<223> OTHER INFORMATION: restriction cassette

<400> SEQUENCE: 58

Ala Leu Glu Asp Pro Gly Lys Leu Pro Ser Glu Lys
1               5                   10

<210> SEQ ID NO 59
<211> LENGTH: 36
<212> TYPE: DNA
<213> ORGANISM: Artificial Sequence
<220> FEATURE:
```

<223> OTHER INFORMATION: restriction cassette

<400> SEQUENCE: 59
gctcttgaag atcccgggaa acttccaagt gaaaaa         36

<210> SEQ ID NO 60
<211> LENGTH: 10
<212> TYPE: PRT
<213> ORGANISM: Artificial Sequence
<220> FEATURE:
<223> OTHER INFORMATION: restriction cassette

<400> SEQUENCE: 60

Val Glu Asp Gly Glu Lys Ala Ala Leu Ala
1               5                   10

<210> SEQ ID NO 61
<211> LENGTH: 30
<212> TYPE: DNA
<213> ORGANISM: Artificial Sequence
<220> FEATURE:
<223> OTHER INFORMATION: restriction cassette

<400> SEQUENCE: 61
gtcgaggacg gcgagaaggc cgccctcgcg         30

<210> SEQ ID NO 62
<211> LENGTH: 12
<212> TYPE: PRT
<213> ORGANISM: Artificial Sequence
<220> FEATURE:
<223> OTHER INFORMATION: restriction cassette

<400> SEQUENCE: 62

Val Glu Asp Gly Glu Asp Ile Lys Ala Ala Leu Ala
1               5                   10

<210> SEQ ID NO 63
<211> LENGTH: 36
<212> TYPE: DNA
<213> ORGANISM: Artificial Sequence
<220> FEATURE:
<223> OTHER INFORMATION: restriction cassette

<400> SEQUENCE: 63
gtcgaggacg gcgaggatat caaggccgcc ctcgcg         36

<210> SEQ ID NO 64
<211> LENGTH: 10
<212> TYPE: PRT
<213> ORGANISM: Artificial Sequence
<220> FEATURE:
<223> OTHER INFORMATION: insertion site

<400> SEQUENCE: 64

Ala Leu Glu Asp Lys Leu Pro Ser Glu Lys
1               5                   10

<210> SEQ ID NO 65
<211> LENGTH: 30
<212> TYPE: DNA
<213> ORGANISM: Artificial Sequence
<220> FEATURE:
<223> OTHER INFORMATION: insertion site

<400> SEQUENCE: 65
gctcttgaag ataaacttcc aagtgaaaaa                                    30

<210> SEQ ID NO 66
<211> LENGTH: 25
<212> TYPE: PRT
<213> ORGANISM: Artificial Sequence
<220> FEATURE:
<223> OTHER INFORMATION: insertion site

<400> SEQUENCE: 66

Ala Leu Glu Asp Pro Arg Phe Tyr Pro Tyr Asp Val Pro Asp Tyr Ala
1               5                   10                  15

Thr Thr Gly Lys Leu Pro Ser Glu Lys
            20                  25

<210> SEQ ID NO 67
<211> LENGTH: 75
<212> TYPE: DNA
<213> ORGANISM: Artificial Sequence
<220> FEATURE:
<223> OTHER INFORMATION: insertion site

<400> SEQUENCE: 67
gctcttgaag atcccaggtt ttatccatac gacgtcccgg actacgccac aactgggaaa    60
cttccaagtg aaaaa                                                     75

<210> SEQ ID NO 68
<211> LENGTH: 115
<212> TYPE: PRT
<213> ORGANISM: Homo sapiens

<400> SEQUENCE: 68

Asn Leu Val Asn Phe His Arg Met Ile Lys Leu Thr Thr Gly Lys Glu
1               5                   10                  15

Ala Ala Leu Ser Tyr Gly Phe Tyr Gly Cys His Cys Gly Val Gly Gly
            20                  25                  30

Arg Gly Ser Pro Lys Asp Ala Thr Asp Arg Cys Cys Val Thr His Asp
        35                  40                  45

Cys Cys Tyr Lys Arg Leu Glu Lys Arg Gly Cys Gly Thr Lys Phe Leu
    50                  55                  60

Ser Tyr Lys Phe Ser Asn Ser Gly Ser Arg Ile Thr Cys Ala Lys Gln
65                  70                  75                  80

Asp Ser Cys Arg Ser Gln Leu Cys Glu Cys Asp Lys Ala Ala Ala Thr
                85                  90                  95

Cys Phe Ala Arg Asn Lys Thr Thr Tyr Asn Lys Lys Tyr Gln Tyr Tyr
                100                 105                 110

Ser Asn Lys
        115